(12) United States Patent
Platzek et al.

(10) Patent No.: US 6,676,928 B2
(45) Date of Patent: Jan. 13, 2004

(54) PERFLUOROALKYL-CONTAINING COMPLEXES WITH POLAR RADICALS, PROCESS FOR THEIR PRODUCTION AND THEIR USE

(75) Inventors: Johannes Platzek, Berlin (DE); Peter Mareski, Berlin (DE); Ulrich Niedballa, Berlin (DE); Bernd Raduechel, Berlin (DE); Hanns-Joachim Weinmann, Berlin (DE); Bernd Misselwitz, Glienicke (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/925,420

(22) Filed: Aug. 10, 2001

(65) Prior Publication Data

US 2002/0076380 A1 Jun. 20, 2002

Related U.S. Application Data

(60) Provisional application No. 60/234,953, filed on Sep. 26, 2000.

(30) Foreign Application Priority Data

Aug. 11, 2000 (DE) .......................... 100 40 858

(51) Int. Cl.$^7$ .................. A61B 5/055; A61K 51/00; C07D 225/00

(52) U.S. Cl. ................. 424/9.363; 424/1.65; 424/9.36; 424/9.364; 424/9.365; 424/9.4; 424/9.42; 540/465; 540/474

(58) Field of Search .................. 424/9.3, 9.36, 424/9.361, 9.363, 9.364, 9.365, 9.4, 1.65, 9.42, 9.44; 540/465, 470, 474

(56) References Cited

FOREIGN PATENT DOCUMENTS

| CA | 2243316 | 7/1997 |
|---|---|---|
| DE | 43 17 588 A1 | 12/1994 |
| DE | 19603033 A | 7/1997 |
| DE | 196 03 033 A1 | 7/1997 |
| DE | 196 08 278 A1 | 8/1997 |
| DE | 197 29 013 A1 | 2/1999 |

*Primary Examiner*—Michael G. Hartley
(74) *Attorney, Agent, or Firm*—Millen, White, Zelano & Branigan, P.C.

(57) ABSTRACT

Perfluoroalkyl-containing complexes with polar radicals of general formula I $$(K)_1\text{-}G\text{-}(Z\text{-}R_f)_m(R)_p \qquad (I)$$

in which R means the polar radical, $R_f$ means a perfluorinated carbon chain, K is a metal complex, and Z represents a linker group,
are suitable for intravenous lymphography, for tumor diagnosis and for infarction and necrosis imaging.

29 Claims, No Drawings

PERFLUOROALKYL-CONTAINING COMPLEXES WITH POLAR RADICALS, PROCESS FOR THEIR PRODUCTION AND THEIR USE

This application claims priority from U.S. Provisional Application No. 60/234,953, filed Sep. 26, 2000, as well as German Application No. 10040858.3, filed Aug. 11, 2000.

DESCRIPTION

The invention relates to the subjects that are characterized in the claims, namely perfluoroalkyl-containing metal complexes with polar radicals of general formula I, process for their production and their use in NMR diagnosis and x-ray diagnosis, radiodiagnosis and radiotherapy, in MRT-lymphography and as blood-pool agents. The compounds according to the invention are quite especially suitable for intravenous lymphography, for tumor diagnosis and for infarction and necrosis imaging.

In nuclear magnetic resonance, the element fluorine is second in importance to the element hydrogen.

1) Fluorine has a high sensitivity of 83% of that of hydrogen.
2) Fluorine has only one NMR-active isotope.
3) Fluorine has a resonance frequency that is similar to hydrogen—fluorine and hydrogen can be measured with the same system.
4) Fluorine is biologically inert.
5) Fluorine does not occur in biological material (exception: teeth) and can therefore be used as a probe or contrast medium against a background that is free of interfering signals.

The effect of these properties is that fluorine occupies a broad space in diagnostic patent literature with magnetic nuclear resonance as a basis: fluorine-19-imaging, functional diagnosis, spectroscopy.

U.S. Pat. No. 4,639,364 (Mallinckrodt) thus proposes trifluoromethanesulfonamides as contrast media for fluorine-19-imaging:

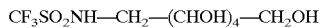

German Patent DE 4203254 (Max-Planck-Gesellschaft), in which an aniline derivative is proposed:

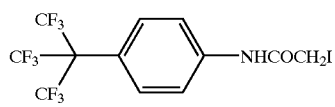

also relates to fluorine-19-imaging.

Fluorine-19-imaging is the subject of Application WO 93/07907 (Mallinckrodt), in which phenyl derivatives are also claimed as contrast media:

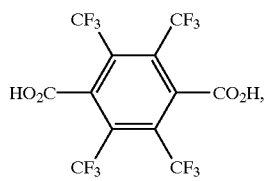

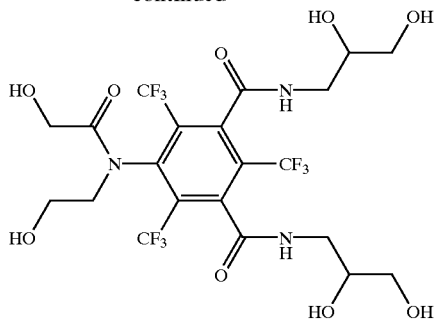

For fluorine-19-imaging, compounds of considerably simpler structure are also claimed. Thus, U.S. Pat. No. 4,586,511 (Children's Hospital Medical Center) mentions perfluoroctylbromide

European Patent EP 307863 (Air Products) mentions perfluoro-15-crown-5-ether

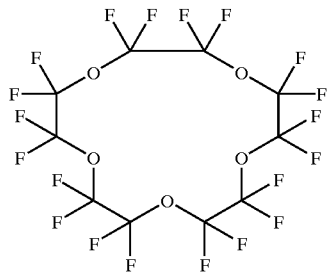

and U.S. Pat. No. 4,588,279 (University of Cincinnati, Children's Hospital Research Foundation) mentions perfluorocarbon compounds such as perfluorocyclonanone or -octane, perfluorinated ethers such as tetrahydrofuran

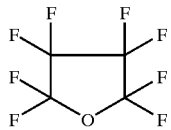

or diethers such as perfluoropropylene glycol-diether

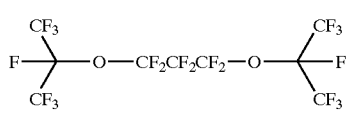

The compounds that are mentioned in Application WO 94/22368 (Molecular Biosystems), e.g.,

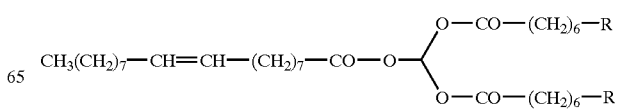

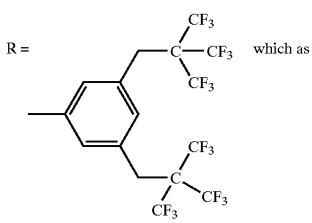 which as fluorine-containing radicals have the perfluorine-1H group or 1H-neopentyl group, are also used for fluorine-19-imaging.

U.S. Pat. No. 5,362,478 (VIVORX) indicates another structural type with expanded diagnostic use, in which the fluorocarbon/polymer shell combination is claimed for imaging purposes. Perfluorononane and human serum albumin are mentioned. This combination proves suitable, moreover, for using the fluorine atom as a probe for local temperature measurement and for determining the partial oxygen pressure.

Perfluorocarbons are also claimed in U.S. Pat. No. 4,586,511 for oxygen determination.

In German Patent DE 4008179 (Schering), fluorine-containing benzenesulfonamides are claimed as pH probes:

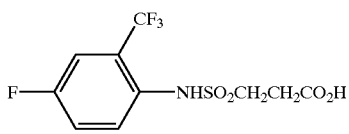

For NMR diagnosis, compounds that contain iodine and fluorine atoms are also claimed as contrast-enhancing agents in WO 94/05335 and WO 94/22368 (both molecular biosystems):

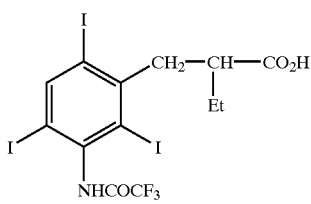

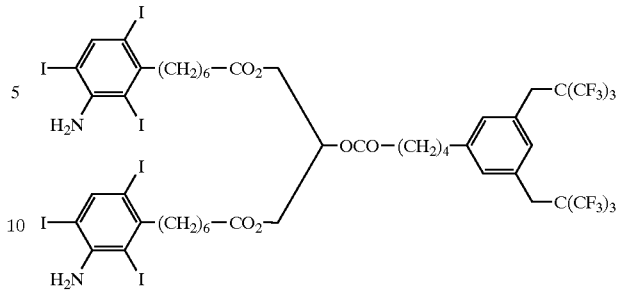

The fluorine-paramagnetic metal ion combination is also claimed for fluorine-19-imaging, specifically for open-chain complexes in WO 94/22368 (Molecular Biosystems) with, e.g.:

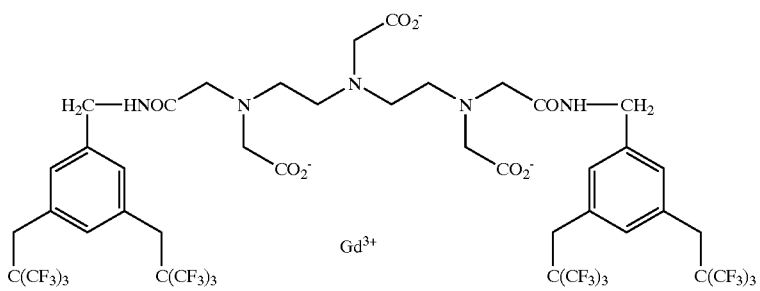

and in EP 292 306 (TERUMO Kabushiki Kaisha) with, e.g.:

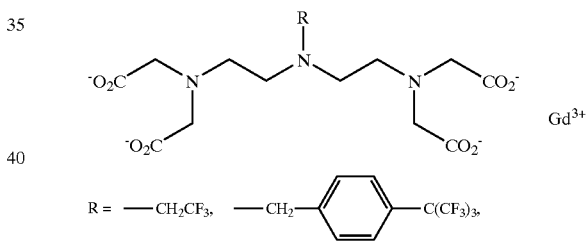

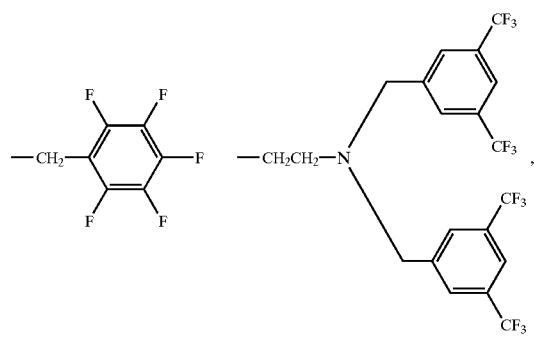

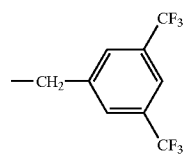

but also for cyclic compounds, as they are mentioned in EP 628 316 (TERUMO Kabushiki Kaisha)

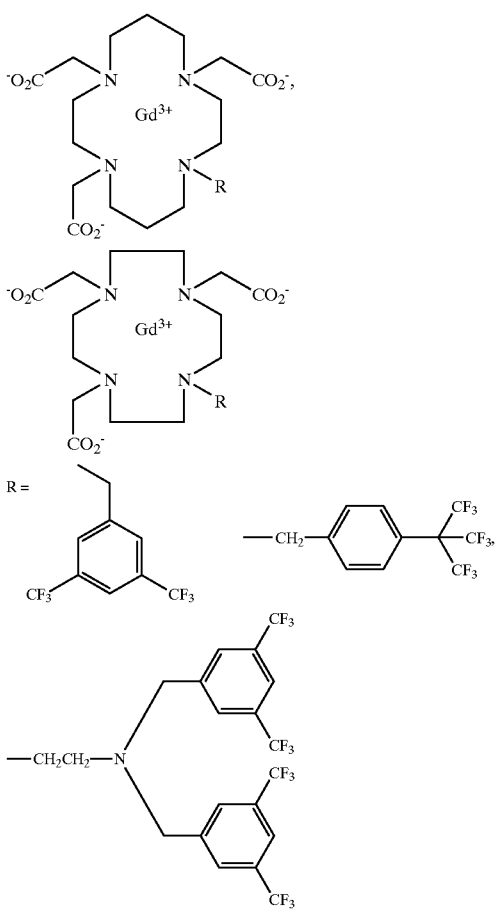

The combination of fluorine atom and rare-earth metal is also claimed for NMR-spectroscopic temperature measurements in DE 4317588 (Schering):

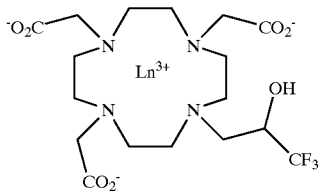

Ln: Rare earths: La, Pr, Dy, Eu

While no interactions occur between the two nuclei in compounds that contain the elements fluorine and iodine, intensive interaction does occur in compounds that contain fluorine and paramagnetic centers (radicals, metal ions) and that are expressed in a shortening of the relaxation time of the fluorine nucleus. The extent of this effect depends on the number of unpaired electrons of the metal ion ($Gd^{3+}>Mn^{2+}>Fe^{3+}>Cu^{2+}$) and on the removal between the paramagnetic ion and the $^{19}F$-atom.

The more unpaired electrons of the metal ion are present and the closer the latter are brought to the fluorine, the greater the shortening of the relaxation time of the fluorine nucleus.

The shortening of the relaxation time as a function of the distance from the paramagnetic ion becomes apparent in all nuclei with an uneven spin number, thus also in the case of protons, and gadolinium compounds are therefore widely used as contrast media in nuclear spin tomography (Magnevist[(R)], Prohance[(R)], Omniscan[(R)], and Dotarem[(R)].

In $^1H$-MR imaging ($^1H$-MRI), however, relaxation time $T^1$ or $T^2$ of the protons, i.e., mainly the protons of water, and not the reaction time of the fluorine nuclei, is measured and used for imaging. The quantitative measurement for the shortening of the relaxation time is relaxivity [L/mmol·s]. Complexes of paramagnetic ions are successfully used for shortening relaxation times. In the following table, the relaxivity of several commercial preparations is indicated:

| | $T^1$ - Relaxivity in Water [1/mmol s, 39° C., 0.47 T] | $T^1$ - Relaxivity in Plasma [1/mmol s, 39° C., 0.47 T] |
| --- | --- | --- |
| MAGNEVIST ® | 3.8 | 4.8 |
| DOTAREM ® | 3.5 | 4.3 |
| OMNISCAN ® | 3.8 | 4.4 |
| PRO HANCE ® | 3.7 | 4.9 |

Only interactions between protons and the gadolinium ion are found in these compounds. For these contrast media in water, a relaxivity of about 4 [1/mmol·s] is thus observed.

Both fluorine compounds for fluorine-19-imaging, in which the shortened relaxation time of the fluorine nucleus is used, and non-fluorine-containing compounds, in which the relaxation time of protons of water is measured, are thus used successfully for MR imaging.

In the introduction of a perfluorocarbon-containing radical into a paramagnetic contrast medium, i.e., in the combination of properties that were previously known as suitable only for fluorine-imaging compounds, the relaxivity that relates to the protons of water also quickly increases, surprisingly enough, with compounds that were used for proton imaging. It now reaches values of 10–50 [1/mmol·s] in comparison to values of between 3.5 and 3.8 [1/mmol·s] as they were already cited for a few commercial products in the table above.

Perfluoroalkyl-containing metal complexes are already known from DE 196 034 033.1. These compounds, however, cannot be used satisfactorily for all applications. Thus, there is still a need for contrast media for the visualization of malignant tumors, lymph nodes and necrotic tissue.

Malignant tumors metastasize in clusters in regional lymph nodes, whereby multiple lymph node stations may also be involved. Lymph node metastases thus are found in about 50–69% of all patients with malignant tumors (Elke, Lymphographie (Lymphography), in: Frommhold, Stender, Thurn (eds.), Radiologische Diagnostik in Klinik und Praxis [Radiological Diagnosis in Clinical Studies and in Practice], Volume IV, Thieme Verlag Stuttgart, 7th Ed., 434–496, 1984).). The diagnosis of a metastatic attack of lymph nodes is of great importance with respect to the treatment and prognosis of malignant types of diseases. With modern imaging methods (CT, US and MRI), lymphogenous evacuations of malignant tumors are detected only inadequately, since in most cases only the size of the lymph node can be used as a diagnostic criterion. Thus, small metastases in non-enlarged lymph nodes (<2 cm) cannot be distinguished from lymph node hyperplasias without a malignant attack (Steinkamp et al., Sonographie und Kernspintomographie: Differentialdiagnostik von reaktiver Lymphknoten-vergröBerung und Lymphknoten-metastasen am Hals [Sonography and Nuclear Spin Tomography: Differential Diagnosis of Reactive Lymph Node Enlargement and Lymph Node Metastasis on the Neck], Radiol. Diagn. 33:158, 1992).

It would be desirable if a distinction could be made when using specific contrast media lymph nodes with metastatic attack and hyperplastic lymph nodes.

Direct x-ray lymphography (injection of an oily contrast medium suspension into a prepared lymph vessel) is known as an invasive method that is used only very rarely and that can visualize only small lymph drainage stations.

Fluorescence-labeled dextrans are also used experimentally in animal experiments to be able to observe lymphatic drainage after their interstitial administration. All commonly used markers for the visualization of lymph tracts and lymph nodes after interstitial/intracutaneous administration have in common the fact that they are substances with particulate character ("particulates," e.g., emulsions and nanocrystal suspensions) or large polymers (see above, WO 90/14846). Based on their inadequate local and systemic compatibility as well as their small lymphatic passageway, which causes inadequate diagnostic efficiency, the previously described preparations still do not prove optimally suitable for indirect lymphography, however.

Since the visualization of lymph nodes is of central importance for the early detection of metastatic attack in cancer patients, there is a great need for lymph-specific contrast medium preparations for diagnosis of corresponding changes of the lymphatic system.

The highest possible contrast medium concentration and high stability are just as desirable as the diagnostically relevant, most uniform possible lymphatic concentration over several lymph stations. The burden on the overall organism should be kept low by quick and complete excretion of the contrast medium. A quick start-up, if possible as early as within a few hours after the administration of contrast media, is important for the radiological practice. Good compatibility is necessary.

Largely for this reason, it is desirable to have available lymph-specific contrast media that in a diagnostic session allow both the primary tumor and a possible lymph node metastasizing to be visualized.

Another important area in medicine is the detection, localization and monitoring of necroses or infarctions. Thus, myocardial infarction is not a stationary process, but rather a dynamic process, which extends over a long period (weeks to months). The disease proceeds in about three phases, which are not strictly separated from one another, but rather are overlapping. The first phase, the development of myocardial infarction, comprises the 24 hours after the infarction, in which the destruction from the subendocardium to the myocardium progresses like a shock wave (wave front phenomenon). The second phase, the already existing infarction, comprises the stabilization of the area in which fiber formation (fibrosis) takes place as a healing process. The third phase, the healed infarction, begins after all destroyed tissue is replaced by fibrous scar tissue. During this period, an extensive restructuring takes place.

Up until now, no precise and reliable process is known that enables the current phase of a myocardial infarction to be diagnosed in a living patient. To evaluate a myocardial infarction, it is of decisive importance to know how large the proportion of the tissue that is lost in the infarction is and at what point the loss took place, since the type of therapy depends on this knowledge.

Infarctions take place not only in the myocardium, but rather also in other tissues, especially in the brain.

While the infarction can be healed to a certain extent, in a necrosis, locally limited tissue death, only the harmful sequelae for the residual organism can be prevented or at least reduced. Necroses can develop in many ways: by traumas, chemicals, oxygen deficiency or by radiation. As in infarction, the knowledge of the extent and type of a necrosis is important for further medical treatment.

Tests to improve the localization of infarctions and necroses by using contrast media in non-invasive processes, such as scintigraphy or nuclear spin tomography, therefore already took place earlier. The literature is full of reports on attempts to use porphyrins for necrosis imaging. The results that are achieved, however, paint a contradictory picture. Winkelman and Hoyes thus describe in Nature, 200, 903 (1967) that manganese-5,10,15,20-tetrakis(4-sulfonatophenyl)-porphyrin (TPPS) selectively accumulates in the necrotic portion of a tumor.

Lyon et al. (Magn. Res. Med. 4, 24 (1987)) observed, however, that manganese-TPPS is dispersed in the body, specifically in the kidney, liver, tumor and only in a small portion of the muscles. In this case, it is advantageous that the concentration in the tumor reaches its maximum only on the fourth day and only after the authors had increased the dose from 0.12 mmol/kg to 0.2 mmol/kg. The authors therefore also speak of a non-specific take-up of TPPS in the tumor. Bockhurst et al. in turn report in Acta Neurochir 60, 347 (1994, Suppl.) that MnTPPS binds selectively to tumor cells.

Foster et al. (J. Nucl. Med. 26, 756 (1985)) in turn found that $^{111}$In-5,10,15,20-tetrakis-(4-N-methyl-pyridinium)-porphyrin (TMPyP) does not accumulate in the necrotic portion, but rather in the living edge layers. It follows from the above that a porphyrin-tissue interaction exists and is obvious but not necessary.

In Circulation Vol. 90, No. 4, part 2, page 1468, Abstract No. 2512 (1994), Ni et al. report that they can visualize infarction areas with a manganese-tetraphenyl-porphyrin (Mn-TPP) and a gadolinium-mesoporphyrin (Gd-MP). In International Patent Application WO 95/31219, both substances were used in infarction and necrosis imaging. Authors Marchal and Ni write (see Example 3) that for the compound Gd-Mp, the metal content of the infarction-kidney was high, similar to that of the non-infarcted organ, but that it was nine times as large for the myocardium in the case of infarcted tissue (Example 1). It was surprising that the ratio of the signal intensities in MRI for infarcted patients was comparatively high in comparison to healthy tissue in both cases with 2.10 or 2.19. Other metalloporphyrins have been described in Application DE 19835082 (Schering AG).

Porphyrins tend to be stored in the skin, which results in a photosensitization. The sensitization can last for days, and even weeks. This in an undesirable side-effect in using porphyrins as diagnostic agents. In addition, the therapeutic index for the porphyrins is only very small, since, e.g., for Mn-TPPS, an action is used only at a dose of 0.2 mmol/kg, but $LD_{50}$ is already approximately 0.5 mmol/kg.

Contrast media for necrosis and infarction imaging that are not derived from the porphyrin skeleton are described in DE 19744003 (Schering AG), DE 19744004 (Schering AG) and WO 99/17809 (EPIX). To date, however, there are still no compounds that can be used satisfactorily as contrast media in infarction and necrosis imaging.

The object of the invention was therefore to make available contrast media that can be used in particular for MRT-lymphography, but also for tumor diagnosis and necrosis and infarction imaging.

The object of the invention is achieved by the perfluoroalkyl-containing complexes with polar radicals of general formula I

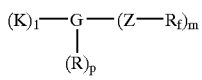
(I)

in which $R_f$ is a perfluorinated, straight-chain or branched carbon chain with the formula $—C_nF_{2n}E$, in which E represents a terminal fluorine, chlorine, bromine, iodine or hydrogen atom, and n stands for numbers 4–30, K stands for a metal complex of general formula II

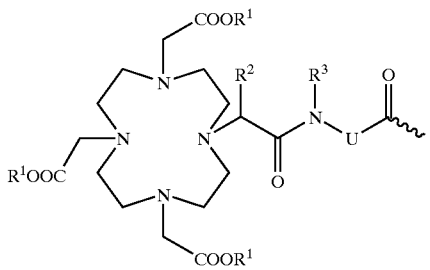
(II)

in which $R^1$ means a hydrogen atom or a metal ion equivalent of atomic numbers 21–29, 31–33, 37–39, 42–44, 49 or 57–83, provided that at least two $R^1$ stand for metal ion equivalents, $R^2$ and $R^3$, independently of one another, represent hydrogen, $C_1$–$C_7$ alkyl, benzyl, phenyl, $—CH_2OH$ or $—CH_2OCH_3$, and U represents $—C_6H_4—O—CH_2$-ω-, $—(CH_2)_{1-5}$-ω, a phenylene group, $—CH_2—NHCO—CH_2—CH(CH_2COOH)—C_6H_4$-ω-, $—C_6H_4—(OCH_2CH_2)_{0-1}—$, $N(CH_2COOH)—CH_2$-ω or a $C_1$–$C_{12}$ alkylene group or a $C_7$–$C_{12}$–$C_6H_4$—O group that is optionally interrupted by one or more oxygen atoms, 1 to 3 —NHCO groups or 1- to 3 —CONH groups and/or is substituted with 1 to 3-$(CH_2)_{0-5}$ COOH groups, whereby ω stands for the binding site to —CO—, or of general formula III

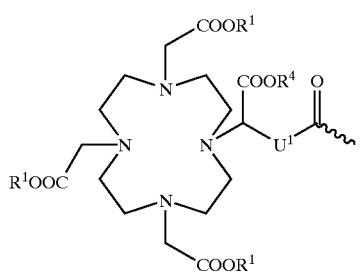
(III)

in which $R^1$ has the above-mentioned meaning, $R^4$ represents hydrogen or a metal ion equivalent that is mentioned under $R^1$, and $U^1$ represents $—C_6H_4—O—CH_2$-ω-, whereby ω means the binding site to —CO— or of general formula IV

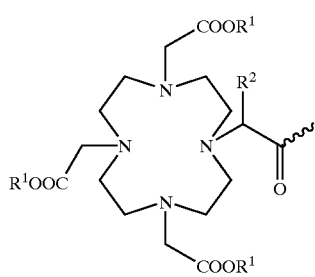
(IV)

in which $R^1$ and $R^2$ have the above-mentioned meaning or of general formula V A or V B

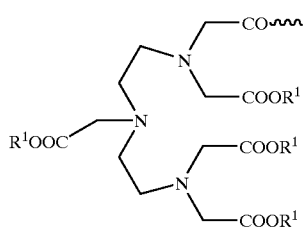
(VA)

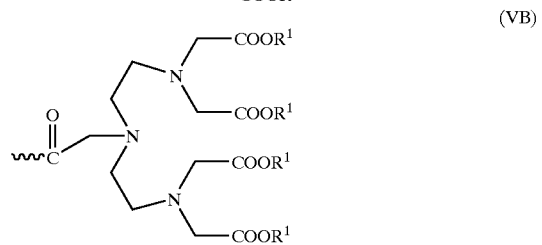
(VB)

in which $R^1$ has the above-mentioned meaning, or of general formula VI

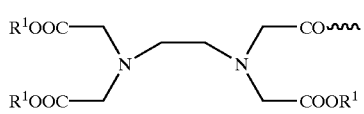
(VI)

in which $R_1$ has the above-mentioned meaning, or of general formula VII

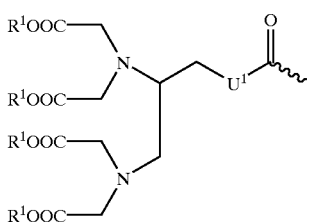
(VII)

in which R¹ has the above-mentioned meaning, and

U¹ represents —C₆H₄—O—CH₂-ω-, whereby ω means the binding site to —CO—, and in radical K, optionally present free acid groups optionally can be present as salts of organic and/or inorganic bases or amino acids or amino acid amides, G represents a radical that is functionalized in at least three places and that is selected from radicals a) to g) below

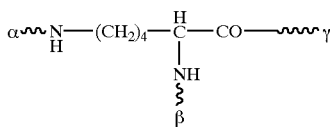
(a)

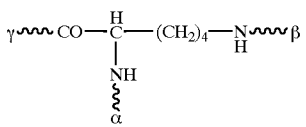
(b)

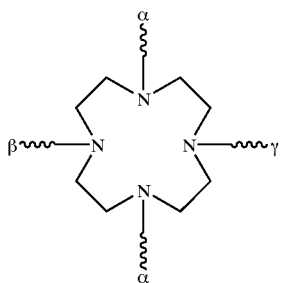
(c)

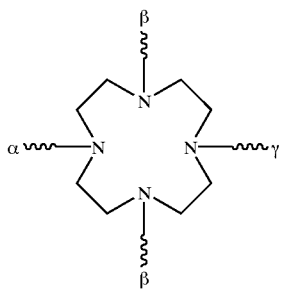
(d)

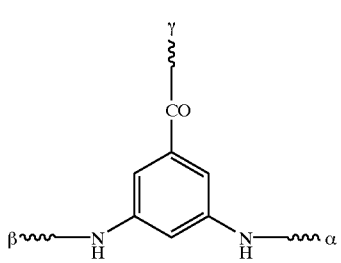
(e)

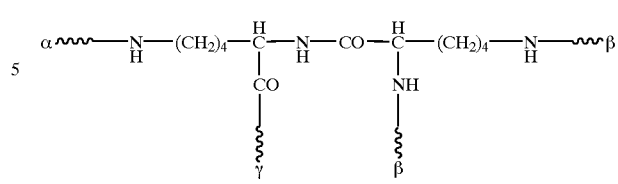
(f)

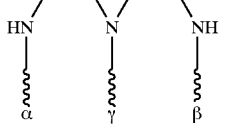
(g)

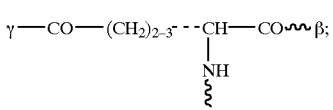
(h)

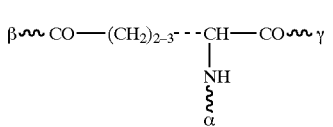
(i)

whereby α means the binding site of G to complex K, β is the binding site of G to radical R and γ represents the binding site of G to radical Z, Z stands for

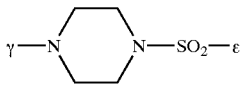

γ-C(O)CH₂O(CH₂)₂-ξ, whereby γ represents the binding site of Z to radical G, and ξ means the binding site of Z to perfluorinated radical $R_f$, R represents a polar radical selected from complexes K of general formulas II to VII, whereby R¹ here means a hydrogen atom or a metal ion equivalent of atomic numbers 20–29, 31–33, 37–39, 42–44, 49 or 57–83, and radicals R², R³, R⁴, U and U¹ have the above-indicated meaning wherein when G means (he residue (c) or (d) and R is selected from general formula II or V, R shall not be identical with K of general formula I if Z stands for γ-C(O)CH₂O(CH₂)-ε or the folic acid radical or R means a carbon chain with 2–30 C-atoms that is bonded via —CO—, SO₂— or a direct bond to radical G, in a straight line or branched, saturated or unsaturated, optionally interrupted by 1–10 oxygen atoms, 1–5 —NHCO groups, 1–5 —CONH groups, 1–2 sulfur atoms, 1–5 —NH groups or 1–2 phenylene groups, which optionally can be substituted with 1–2 OH groups, 1–2 NH₂ groups, 1–2 —COOH groups, or 1–2 —SO₃H groups, or optionally substituted with 1–8 OH groups, 1–5 —COOH groups, 1–2 SO₃H groups, 1–5 NH₂ groups, 1–5 C₁–C₄ alkoxy groups, and l, m, p, independently of one another, mean the whole numbers 1 or 2.

If the compound according to the invention is intended for use in NMR diagnosis, the metal ion of the signal-transmitting group must be paramagnetic. These are especially the divalent and trivalent ions of the elements of atomic numbers 21–29, 42, 44 and 58–70. Suitable ions are, for example, the chromium(III) ion, iron(II) ion, cobalt(II) ion, nickel(II) ion, copper(II) ion, praseodymium(III) ion, neodymium(III) ion, samarium(III) ion and ytterbium(III) ion. Because of their strong magnetic moment, gadolinium (III), terbium(III), dysprosium(III), holmium(III), erbium (III), iron(III) and manganese(II) ions are especially preferred. erbium(III), iron(III) and manganese(II) ions are especially preferred.

For the use of the compounds according to the invention in nuclear medicine (radiodiagnosis and radiotherapy), the metal ion must be radioactive. For example, radioisotopes of the elements with atomic numbers 27, 29, 31–33, 37–39, 43, 49, 62, 64, 70, 75 and 77 are suitable. Technetium, gallium, indium, rhenium, and yttrium are preferred.

If the compound according to the invention is intended for use in x-ray diagnosis, the metal ion is preferably derived from an element of a higher atomic number to achieve a sufficient absorption of x-rays. It was found that diagnostic agents that contain a physiologically compatible complex salt with metal ions of elements of atomic numbers 25, 26 and 39 as well as 57–83 are suitable for this purpose.

Manganese(II), iron(II), iron(III), praseodymium(III), neodymium(III), samarium(III), gadolinium(III), ytterbium (III) or bismuth(III) ions, especially dysprosium(III) ions and yttrium(III) ions, are preferred.

Acidic hydrogen atoms that are optionally present in $R^1$, i.e., those that have not been substituted by the central ion, can optionally be replaced completely or partially by cations of inorganic and/or organic bases or amino acids or amino acid amides.

Suitable inorganic cations are, for example, the lithium ion, the potassium ion, the calcium ion and especially the sodium ion. Suitable cations of organic bases are, i.a., those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, arginine, and ornithine as well as the amides of otherwise acidic or neutral amino acids.

Especially preferred compounds of general formula I are those with macrocycle K of general formulas II, III, VB or VII.

Radical U in metal complex K preferably means $-CH_2-$ or $C_6H_4-O-CH_2-\omega$, whereby $\omega$ stands for the binding site to $-CO-$.

Alkyl groups $R^2$ and $R^3$ in the macrocycle of general formula II can be straight-chain or branched. By way of example, methyl, ethyl, propyl, isopropyl, n-butyl, 1-methyl-propyl, 2-methylpropyl, n-pentyl, 1-methylbutyl, 2-methylbutyl, 3-methylbutyl, 1,2-dimethylpropyl can be mentioned. $R^2$ and $R^3$, independently of one another, preferably mean hydrogen or $C_1-C_4$ alkyl.

In a quite especially preferred embodiment, $R^2$ stands for methyl and $R^3$ stands for hydrogen.

The benzyl group or the phenyl group $R^2$ or $R^3$ in macrocycle K of general formula II can also be substituted in the ring.

Polar radical R in general formula I means complex K in a preferred embodiment, whereby the latter can also be a $Ca^{2+}$ complex preferably in addition to a $Gd^{3+}$ complex or an $Mn^{2+}$ complex. Complexes K of general formulas II, III, VA or VII are especially preferred as polar radicals R. The latter as $R^1$ quite especially preferably exhibit a metal ion equivalent of atomic numbers 20, 25 or 64.

In another preferred embodiment, polar radical R has the following meanings:

—C(O)CH$_2$CH$_2$SO$_3$H
—C(O)CH$_2$OCH$_2$CH$_2$OCH$_2$CH$_2$OH
—C(O)CH$_2$OCH$_2$CH$_2$OH
—C(O)CH$_2$OCH$_2$CH(OH)CH$_2$OH
—C(O) CH$_2$NH—C(O)CH$_2$COOH
—C(O)CH$_2$CH(OH)CH$_2$OH
—C(O) CH$_2$OCH$_2$COOH
—SO$_2$CH$_2$CH$_2$COOH
—C(O)—C$_6$H$_3$—(m-COOH)$_2$
—C(O)CH$_2$O(CH$_2$)$_2$—C$_6$H$_3$—(m—CCOH)$_2$
—C(O)CH$_2$O—C$_6$H4—m—SO$_3$H
—C(O)CH$_2$NHC(O)CH$_2$NHC(O) CH$_2$OCH$_2$COOH
—C(O)CH$_2$OCH$_2$CH$_2$OCH$_2$COOH
—C(O)CH$_2$OCH$_2$CH(OH)CH$_2$O—CH$_2$CH$_2$OH
—C(O)CH$_2$OCH$_2$CH(OH)CH$_2$OCH$_2$—CH(OH)—CH$_2$OH
—C(O)CH$_2$SO$_3$H
—C(O)CH$_2$CH$_2$COOH
—C(O)CH(OH)CH(OH)CH$_2$OH
—C(O)CH$_2$O[(CH$_2$)$_2$O]$_{1-9}$—CH$_3$
—C(O)CH$_2$O[(CH$_2$)$_2$O]$_{1-9}$—H
—C(O)CH$_2$OCH(CH$_2$OH)$_2$
—C(O)CH$_2$OCH(CH$_2$OCH$_2$COOH)$_2$
—C(O)—C$_6$H$_3$—(m—OCH$_2$COOH)$_2$
—CO—CH$_2$O—(CH$_2$)$_2$O(CH$_2$)$_2$O—(CH$_2$)$_2$O(CH$_2$)$_2$OCH$_3$ preferably —C(O)CH$_2$O [(CH$_2$)$_2$O]$_4$—CH$_3$.

In another preferred embodiment, polar radical R means the folic acid radical.

Of the compounds of general formula I according to the invention, in addition those are preferred in which $R_f$ means —C$_n$F$_{2n+1}$. n preferably stands for the numbers 4–15. Quite especially preferred are radicals —C$_4$F$_9$, —C$_6$F$_{13}$, —C$_8$F$_{17}$, C$_{12}$F$_{25}$ and —C$_{14}$F$_{29}$ as well as the radicals of the compounds that are mentioned in the examples.

Radical G that is functionalized in at least three places in general formula I, which represents the "skeleton," means lysine radical (a) or (b) in a preferred embodiment of the invention.

Z means the linker that is indicated in general formula I, whereby the radical

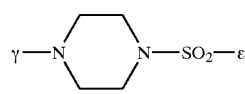

is preferred.

The perfluoroalkyl-containing metal complexes with polar radicals of general formula I

in which K, G, R, Z, $R_f$, l, m and p have the above-indicated meaning, are produced, in a way that is known in the art, by a carboxylic acid of general formula IIa

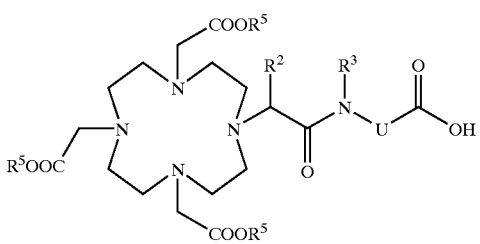
(IIa)

in which $R^5$ means a metal ion equivalent of atomic numbers 21–29, 31–33, 37–39, 42–44, 49 or 57–83 or a carboxyl protective group, and $R^2$, $R^3$ and U have the above-mentioned meaning, or a carboxylic acid of general formula IIIa

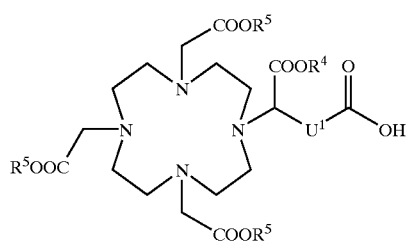
(IIIa)

in which $R^4$, $R^5$, and $U^1$ have the above-mentioned meaning or a carboxylic acid of general formula IVa

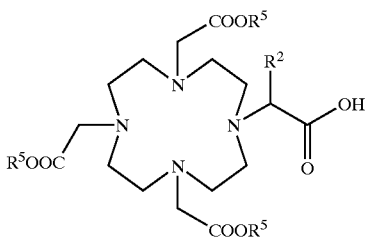
(IVa)

in which $R^5$ and $R^2$ have the above-mentioned meaning or a carboxylic acid of general formula Va or Vb

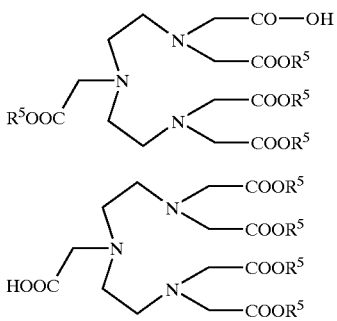
(Va)
(Vb)

in which $R^5$ has the above-mentioned meaning or a carboxylic acid of general formula VIa

(VIa)

in which $R^5$ has the above-mentioned meaning or a carboxylic acid of general formula VIIa

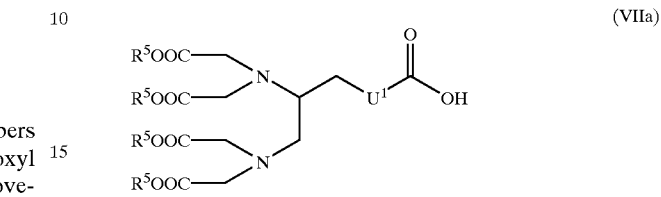
(VIIa)

in which $R^5$ and $U^1$ have the above-mentioned meanings, being reacted in optionally activated form with an amine of general formula VIII

(VIII)

in which G, R, Z, $R_f$, m and p have the indicated meaning, in a coupling reaction and optionally subsequent cleavage of optionally present protective groups into a metal complex of general formula I, or if $R^5$ has the meaning of a protective group, being reacted after cleavage of these protective groups in a subsequent step in a way that is known in the art with at least one metal oxide or metal salt of an element of atomic numbers 21–29, 31–33, 37–39, 42 –44, 49 or 57–83, and then, if desired, optionally present, acidic hydrogen atoms are substituted by cations of inorganic and/or organic bases, amino acid or amino acid amides.

The carboxylic acids of general formulas IIa to VIIA that are used are either known compounds or are produced according to the process described in the examples. Thus, the production of carboxylic acids of general formula IIa is known from DE 196 52 386. The production of carboxylic acids of general formula IIIa can be carried out analogously to Example 4 of this application. The production of the carboxylic acids of general formula IVa can be derived from DE 197 28 954.

A precursor for compounds of general formula VA is $N^3(2,6\text{-dioxomorpholinoethyl})\text{-}N^6\text{-}$(ethoxycarbonylmethyl)-3,6-diaza-octanedioic acid, which is described in EP 263 059.

The compounds of general formula VB are derived from the isomeric diethylenetriamine-pentaacetic acid, which binds via the acetic acid that is on the center N atom. This DTPA is described in Patents DE 195 07 819 and DE 195 08 058.

Compounds of general formula VI are derived from N-(carboxymethyl)-N-[2-(2,6-dioxo-4-morpholinyl)-ethyl]-glycine, whose production is described in J. Am. Oil. Chem. Soc. (1982), 59 (2), 104–107.

Compounds of general formula VII are derived from 1-(4-carboxymethoxybenzyl)-ethylenediamine tetraacetic acid, whose production was described in U.S. Pat. No. 4,622,420.

The production of amines of general formula VIII is described in detail in the examples of this application and can be carried out analogously to the processes described in the examples.

It has been shown that the metal complexes according to the invention are especially suitable for NMR diagnosis and x-ray diagnosis, but also for radiodiagnosis and radiotherapy. The subject of the invention is therefore also the use of the perfluoroalkyl-containing metal complexes according to the invention with polar radicals for production of contrast media for use in NMR diagnosis and x-ray diagnosis, especially for lymphography, for tumor diagnosis, and for infarction imaging and necrosis imaging, as well as in radiodiagnosis and radiotherapy. The compounds according to the invention are extremely well suited for use in interstitial lymphography and especially in intravenous lymphography. In addition, they can also be used for visualization of the vascular space (blood-pool agents).

Subjects of the invention are also pharmaceutical agents that contain at least one physiologically compatible compound according to the invention, optionally with the additives that are commonly used in galenicals.

The compounds of this invention are distinguished by a very good systemic compatibility and a high lymph node concentration in three successive lymph node stations (which is important especially for i.v. lymphography). They are thus especially well suited for use in MRT lymphography.

The compounds according to the invention are also extremely well suited for detecting and localizing vascular diseases, since they are dispersed exclusively in the latter in the administration in the intravascular space. The compounds according to the invention make it possible, with the help of nuclear spin tomography, to distinguish between tissue that is well supplied with blood and tissue that is poorly supplied with blood and thus to diagnose an ischemia. Because of its anemia, infarcted tissue can also be distinguished from surrounding healthy or ischemic tissue, when the contrast media according to the invention are used. This is of special importance if the point is, e.g., to distinguish a myocardial infarction from an ischemia.

Compared to the macromolecular compounds previously used as blood-pool agents, such as, for example, Gd-DTPA-polylysine, the compounds according to the invention also show a higher $T^1$-relaxivity and thus are distinguished by an increase of signal intensity in NMR imaging. Since in addition they have an extended retention in the blood space, they can also be administered in relatively small doses (of, e.g., $\leq 50$ $\mu$mol of Gd/l of body weight). The compounds according to the invention are primarily quickly and as completely as possible eliminated from the body, however.

It was also shown that the compounds according to the invention accumulate in areas with elevated vascular permeability, such as, e.g., in tumors; they make it possible to make statements on the perfusion of tissues, provide the possibility of determining the blood volumes in tissues, to selectively shorten the relaxation times or densities of the blood and to graphically visualize the permeability of blood vessels. Such physiological data cannot be obtained by the use of extracellular contrast media, such as, e.g., Gd-DTPA (Magnevist$^{(R)}$). From these considerations also arise their uses in modern imaging processes nuclear spin tomography and computer tomography: specific diagnosis of malignant tumors, early therapy control in cytostatic, antiphlogistic or vasodilatative therapy, early detection of underperfused areas (e.g., in the myocardium); angiography in vascular diseases, and detection and diagnosis of sterile or infectious inflammations.

The production of the pharmaceutical agents according to the invention is carried out in a way that is known in the art by the complex compounds according to the invention—optionally with the addition of the additives that are commonly used in galenicals—being suspended or dissolved in aqueous medium and then the suspension or solution optionally being sterilized. Suitable additives are, for example, physiologically harmless buffers (such as, for example, tromethamine), additives of complexing agents (such as, for example, diethylenetriaminepentaacetic acid) or weak complexes or the Ca-complexes that correspond to the metal complexes according to the invention or—if necessary—electrolytes such as, for example, sodium chloride or—if necessary—antioxidants, such as, for example, ascorbic acid.

If suspensions or solutions of the agents according to the invention in water or physiological hydrochloric acid solution are desired for enteral or parenteral administration or other purposes, they are mixed with one or more adjuvant(s) that are commonly used in galenicals [for example, methyl cellulose, lactose, mannitol] and/or surfactant(s) [for example, lecithins, Tween$^{(R)}$, Myrj$^{(R)}$] and/or flavoring substance(s) for taste correction [for example, ethereal oils].

Basically, it is also possible to produce the pharmaceutical agents according to the invention without isolating the complexes. In any case, special care must be used to carry out the chelation so that the complexes according to the invention are practically free of non-complexed metal ions that have a toxic effect.

This can be ensured, for example, with the aid of color indicators, such as xylenol orange, by control titrations during the production process. The invention therefore also relates to a process for the production of the complex compounds and their salts. As a final precaution, there remains purification of the isolated complex.

In the in-vivo administration of the agents according to the invention, the latter can be administered together with a suitable vehicle, such as, for example, serum or physiological common salt solution and together with another protein, such as, for example, human serum albumin (HSA).

The agents according to the invention are usually administered parenterally, preferably i.v. They can also be administered intravascularly or interstitially/intracutaneously depending on whether bodily vessels or tissue are to be studied.

The pharmaceutical agents according to the invention preferably contain 0.1 $\mu$mol–2 mol/l of the complex and are generally dosed in amounts of 0.0001–5 mmol/kg.

The agents according to the invention meet the many requirements for suitability as contrast media for nuclear spin tomography. After oral or parenteral administration, they are thus extremely well suited for enhancing the informational value of the image that is obtained with the aid of a nuclear spin tomograph. They also show the high effectiveness that is necessary to load the body with the smallest possible amount of foreign substances and the good compatibility that is necessary to maintain the non-invasive character of the studies.

The good water solubility and low osmolality of the agents according to the invention make it possible to produce highly concentrated solutions, so as to keep the volume burden of the circulatory system within reasonable limits and to offset the dilution by bodily fluids. In addition, the agents according to the invention show not only a high stability in vitro, but also a surprisingly high stability in vivo, so that a release or an exchange of the ions—which are inherently toxic—and which are bonded to the complexes can take place only extremely slowly within the time in which the new contrast media are completely excreted again.

In general, the agents according to the invention for use as NMR diagnostic agents are dosed in amounts of 0.001–5 mmol/kg, preferably 0.005–0.5 mmol/kg.

The complex compounds according to the invention also can advantageously be used as susceptibility reagents and as shift reagents for in-vivo-NMR spectroscopy.

Based on their advantageous radioactive properties, and the good stability of the complex compounds contained therein, the agents according to the invention are also suitable as radiodiagnostic agents. Details of such a use and dosage are described in, e.g., "Radiotracers for Medical Applications," CRC-Press, Boca Raton, Fla.

The compounds and agents according to the invention can also be used in positron-emission tomography, which uses positron-emitting isotopes, such as, e.g., $^{43}$Sc, $^{44}$Sc, $^{52}$Fe, $^{55}$Co, $^{68}$Ga and $^{86}$Y (Heiss, W. D.; Phelps, M. E.; Positron Emission Tomography of Brain, Springer Verlag Berlin, Heidelberg, N.Y. 1983).

The compounds according to the invention are also suitable, surprisingly enough, for differentiating malignant and benign tumors in areas without blood-brain barriers.

They are also distinguished in that they are completely eliminated from the body and thus are well-tolerated.

Since the substances according to the invention accumulate in malignant tumors (no diffusion in healthy tissue, but high permeability of tumor vessels), they can also support the radiation therapy of malignant tumors. The latter is distinguished from the corresponding diagnosis only by the amount and type of the isotope used. The purpose in this case is the destruction of tumor cells with high-energy shortwave radiation with as small a range of action as possible. For this purpose, interactions of the metals (such as, e.g., iron or gadolinium) that are contained in the complexes are used with ionizing radiation (e.g., x-rays) or with neutron rays. By this effect, the local radiation dose at the site where the metal complex is located (e.g., in tumors) is significantly increased. To produce the same radiation dose in malignant tissue, the radiation exposure for healthy tissue can be considerably reduced when using such metal complexes and thus side-effects imposing a burden for the patients are avoided. The metal-complex-conjugates according to the invention are therefore also suitable as radiosensitizing substances in radiation therapy of malignant tumors (e.g., use of Mossbauer effects or in neutron capture therapy). Suitable β-emitting ions are, for example, $^{46}$Sc, $^{47}$Sc, $^{48}$Sc, $^{72}$Ga, $^{73}$Ga and 90Y. Suitably short half-lives that have α-emitting ions are, for example, $^{211}$Bi, $^{212}$Bi, $^{213}$Bi and $^{214}$Bi whereby $^{212}$Bi is preferred. A suitable photon- and electron-emitting ion is "$^{158}$Gd, which can be obtained from $^{157}$Gd by neutron capture.

If the agent according to the invention is intended for use in the variant of radiation therapy proposed by R. L. Mills et al. (Nature Vol. 336, (1988), p. 787), the central ion must be derived from a Mossbauer isotope, such as, for example, $^{57}$Fe or $^{151}$Eu.

In the in-vivo administration of the agents according to the invention, the latter can be administered together with a suitable vehicle, such as, for example, serum, or physiological common salt solution and together with another protein, such as, for example, human serum albumin. In this case, the dosage depends on the type of cellular disorder, the metal ion that is used and the type of imaging method.

The agents according to the invention are usually administered parenterally, preferably i.v. They can also—as already discussed—be administered intravascularly or interstitially/intracutaneously depending on whether bodily vessels or tissue are to be studied.

The agents according to the invention are extremely well suited as x-ray contrast media, whereby it is especially to be emphasized that no displays of the anaphylaxis-like reactions known from the iodine-containing contrast media can be detected in biochemical-pharmacological studies with them. Because of the advantageous absorption properties in the areas of higher tube voltages, they are especially valuable for digital subtraction techniques.

In general, the agents according to the invention for use as x-ray contrast media analogously to the meglumine-diatrizoate example are dosed in amounts of 0.1–5 mmol/kg, preferably 0.25–1 mmol/kg.

In particular, higher blood concentrations are achieved with the compounds according to the invention than with extracellular contrast media. They are dispersed after i.v. administration only into the intravascular space and thus have a decisive advantage compared to the extracellular contrast media.

Embodiments

EXAMPLE 1a

2-N-trifluoroacetyl-6-N-benzyloxycarbonyl-lysine 100 g (356.7 mmol) of 6-N-benzyloxycarbonyl-lysine is dissolved in a mixture that consists of 1000 ml of trifluoroacetic acid ethyl ester/500 ml of ethanol, and it is stirred for 24 hours at room temperature. It is evaporated to the dry state, and the residue is crystallized from diisopropyl ether.

| Yield: | 128.9 g (96% of theory) of a colorless, crystalline powder. | | | |
|---|---|---|---|---|
| Elementary analysis: | | | | |
| Cld: | C 51.07 | H 5.09 | F 15.14 | N 7.44 |
| Fnd: | C 51.25 | H 5.18 | F 15.03 | N 7.58 |

EXAMPLE 1b

2-N-trifluoroacetyl-6-N-benzyloxycarbonyl-lysine-[1-(4-perfluorooctylsulfonyl)Piperazine]-amide 164.2 g (0.664 mmol) of EEDQ (2-ethoxy-1,2-dihydroquinoline-1-carboxylic acid ethyl ester) is added at 0° C. to 125 g (332 mmol) of the title compound of Example 1a and 188.7 g (332 mmol) of 1-perfluorooctylsulfonyl-piperazine (produced according to DE 19603033) in 800 ml of tetrahydrofuran, and it is stirred overnight at room temperature. It is evaporated to the dry state in a vacuum and chromatographed on silica gel (mobile solvent: dichloromethane/methanol=20:1).

| Yield: | 286 g (93% of theory) of a colorless solid. | | | |
|---|---|---|---|---|
| Elementary analysis: | | | | |
| Cld: | C 36.30 | H 2.83 | F 41.01 | N 6.05 | S 3.46 |
| Fnd: | C 36.18 | H 2.94 | F 40.87 | N 5.98 | S 3.40 |

EXAMPLE 1c

6-N-benzyloxycarbonyl-lysine-[1-(4-perfluorooctylsulfonyl)-piperazine]-amide

Ammonia gas is introduced at 0° C. for one hour into a solution that consists of 280 g (302.2 mmol) of the title compound of Example 1b in 2000 ml of ethanol. It is then stirred for four hours at 0" C. It is evaporated to the dry state, and the residue is absorptively precipitated from water. The solid is filtered off and dried in a vacuum (50° C.)

| Yield: | 243.5 g (97% of theory) of an amorphous solid. | | | | |
|---|---|---|---|---|---|
| Elementary analysis: | | | | | |
| Cld: | C 37.60 | H 3.23 | F 38.89 | N 6.75 | S 3.86 |
| Fnd: | C 37.15 | H 3.33 | F 38.78 | N 6.68 | S 3.81 |

EXAMPLE 1d
6-N-tenzyloxycarbonyl-2-N-(3,6,9,12,15-pentaoxahexadecanoyl)-lysine[1-(4-perfluorooctylsulfonyl)-piperazine]-amide A solution that consists of 19.93 g (70 mmol) of 3,6,9,12,15-pentaoxahexadecanoic acid chloride in 50 ml of dichloromethane is added in drops at 0° C. to 50 g (60.20 mmol) of the title compound of Example 1c and 7.10 g (70 mmol) of triethylamine, dissolved in 350 ml of dichloromethane, and it is stirred for three hours at 0° C. 200 ml of 5% aqueous hydrochloric acid is added, and it is stirred for 5 minutes at room temperature. The organic phase is separated, dried on magnesium sulfate and evaporated to the dry state in a vacuum. The residue is chromatographed on silica gel (mobile solvent: dichloromethane/acetone=15:1).

| Yield: | 53.7 g (93% of theory) of a colorless, viscous oil. | | | | |
|---|---|---|---|---|---|
| Elementary analysis: | | | | | |
| Cld: | C 33.83 | H 4.94 | F 3.34 | N 5.84 | S 33.69 |
| Fnd: | C 33.75 | H 5.05 | F 3.29 | N 5.78 | S 33.75 |

EXAMPLE 1e
2-N-(3,6,9,12,15-pentaoxahexadecanoyl)-lysine[1-(4-perfluorooctylsulfonyl)-piperazine]-amide 50 g (52.15 mmol) of the title compound of Example id is dissolved in 500 ml of ethanol, and 6 g of palladium catalyst (10% Pd/C) is added. It is hydrogenated at room temperature. Catalyst is filtered out, and the filtrate is evaporated to the dry state in a vacuum.

| Yield: | 43.0 g (quantitative) of a colorless solid. | | | | |
|---|---|---|---|---|---|
| Elementary analysis: | | | | | |
| Cld: | C 27.68 | H 5.01 | F 39.17 | N 6.79 | S 3.89 |
| Fnd: | C 27.60 | H 5.13 | F 39.09 | N 6.68 | S 3.81 |

EXAMPLE 1f
6-N-[1,4,7-tris(Carboxylatomethyl)-1,4,7,10-tetraazacyclododecane-10-(Pentanoyl-3-aza-4-oxo-5-methyl-5-yl)-2-N-(3,6,9,12,15-pentaoxahexadecanoyl)-lysine[1-(4-perflucrooctylsulfonyl)-piperazine]-amide, Gd-complex 20 g (24.25 mmol) of the title compound of Example 1e, 2.79 g (24.25 mmol) of N-hydroxysuccinimide, 2.12 g (50 mmol) of lithium chloride and 15.27 g (24.25 mmol) of 1,4,7-tris(Carboxylatomethyl)-10-[(3-aza-4-oxo-5-methyl-5-yl)]-pentanoic acid]-1,4,7,10-tetraazacyclododecane, Gd-complex are dissolved in 200 ml of dimethyl sulfoxide while being heated slightly. At 10° C., 8.25 g (40 mmol) of N,N-dicyclohexylcarbodiimide is added, and it is then stirred overnight at room temperature. The solution is poured into 3000 ml of acetone and stirred for 10 minutes. The precipitated solid is filtered off and then purified by chromatography. (silica gel RP-18, mobile solvent: gradient that consists of water/ethanol/acetonitrile).

| Yield: | 28.21 g (81% of theory) of a colorless solid. | | | | | |
|---|---|---|---|---|---|---|
| Water content: | 11.0% | | | | | |
| Elementary analysis | | | | | | |
| (relative to anhydrous substance): | | | | | | |
| Cld: | C 31.78 | H 4.84 | F 22.49 | N 8.78 | S 2.23 | Gd 10.95 |
| End: | C 31.74 | H 4.98 | F 22.39 | N 8.69 | S 2.15 | Gd 10.87 |

EXAMPLE 2a
6-N-[3,9-bis(t-butyloxycarbonylmethyl)-3,6,9-triazaundecane-1,11-dicarboxylic Acid Bis(t-butylester)-6-carbonylmethyl]-2-N-[3,6,9,12,15-pentaoxahexadecanoyl)-lysine-[1-(4-perfluorooctylsulfonyl)-piperazine]-amide 8.25 g (40 mmol) of N,N-dicyclohexylcarbodiimide is added at 0° C. to a solution that consists of 20 g (24.08 mmol) of the title compound of Example 1e, 14.88 g (24.08 mmol) of 3,9-bis(t-butyloxycarbonylmethyl-3,6,9-triazaundecane-1,11-dicarboxylic acid-bis(t-butylester) and 2.77 g (24.08 mmol) of N-hydroxysuccinimide, dissolved in 150 ml of dimethylformamide. It is stirred for 3 hours at 0° C., then overnight at room temperature. Precipitated urea is filtered out, the filtrate is evaporated to the dry state in a vacuum and chromatographed on silica gel (mobile solvent= dichloromethane/ethanol=20:1).

| Yield: | 31.61 g (91% of theory) of a viscous oil. | | | | |
|---|---|---|---|---|---|
| Elementary analysis: | | | | | |
| Cld: | C 40.80 | H 6.71 | F 22.39 | N 6.80 | S 2.22 |
| Fnd: | C 40.72 | H 6.82 | F 22.30 | N 6.75 | S 2.14 |

EXAMPLE 2b
6-N-[6-carbonylmethyl-3,9-bis(Carboxylatomethyl)-3,6,9-triazaundecanedicarboxylic Acid-1-carboxy-11-carboxylato-]-2-N-(3,6,9,12,15-penatoxahexadecanoyl)-lysine-[1-(4-perfluorooctylsulfonyl)-piperazine]-amide, Gd-complex, Sodium Salt 30 g (20.8 mmol) of the title compound of Example 2a is dissolved in 300 ml of trifluoroacetic acid and stirred for 5 hours at room temperature. It is evaporated to the dry state, the residue is taken up in 300 ml of water and set at pH 2.5 with 10% aqueous NaOH. Then 3.77 g (10.4 mmol) of gadolinium oxide is added, and it is stirred for 3 hours at 60° C. It is allowed to reach room temperature and set at pH 7.4 with sodium hydroxide solution. It is evaporated to the dry state, and the residue is purified on silica gel RP-18. (Mobile solvent: gradient that consists of water/acetonitrile).

| Yield: | 19.18 g (67% of theory) of a colorless, amorphous solid. | | | | | |
|---|---|---|---|---|---|---|
| Water content: | 9.8% | | | | | |
| Elementary analysis | | | | | | |
| (relative to anhydrous substance): | | | | | | |
| Cld: | C 28.80 | H 4.25 | F 23.47 | N 7.12 | S 2.33 | Gd 11.48 | Na 1.67 |
| Fnd: | C 28.67 | H 4.34 | F 23.38 | N 7.03 | S 2.27 | Gd 11.37 | Na 1.74 |

EXAMPLE 3a
Lysine-[1-(4-perfluorooctylsulfonyl-piperazine]-amide 20 g (24.08 mmol) of the title compound of Example 1c is dissolved in 300 ml of ethanol, and 4 g of palladium catalyst (10% Pd/C) is added. It is hydrogenated at room temperature. Catalyst is filtered out, and the filtrate is evaporated to the dry state in a vacuum.

Yield: 16.77 g (quantitative) of a colorless solid.
Elementary analysis:

| | | | | | |
|---|---|---|---|---|---|
| Cld: | C 31.04 | H 3.04 | F 46.38 | N 8.04 | S 4.60 |
| Fnd: | C 30.97 | H 3.15 | F 46.31 | N 7.98 | S 4.51 |

EXAMPLE 3b
2,6-N,N'-bis[1,4,7-tris(Carboxylatomethyl)-1,4,7,10-tetraazacyclododecane-10-(Pentanoyl-3-aza-4-oxo-5-methyl-5-yl)]-lysine-[1-(4-perfluorooctylsulfonyl-piperazine]-amide, Gd-complex 10 g (14.36 mmol) of the title compound of Example 3a, 3.34 g (29 mmol) of N-hydroxysuccinimide, 2.54 g (mmol) of lithium chloride and 18.26 g (29 mmol) of 1,4,7-tris(Carboxylatomethyl)-10-(3-aza-4-oxo-5-methyl-5yl)-1,4,7,10-tetraazacyclododecane-Gd-complex are dissolved in 200 ml of dimethyl sulfoxide while being heated slightly. At 10° C., 12.38 g (60 mmol) of N,N-dicyclohexylcarbodiimide is added, and it is then stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 19.02 g (69% of theory) of a colorless solid.
Water content: 11.3%
Elementary analysis
(relative to anhydrous substance):

| | | | | | | |
|---|---|---|---|---|---|---|
| Cld: | C 35.03 | H 4.04 | F 16.82 | N 10.21 | S 1.67 | Gd 16.38 |
| Fnd: | C 34.96 | H 4.13 | F 16.74 | N 10.16 | S 1.61 | Gd 16.33 |

EXAMPLE 4a
2-[4-(3-oxapropionic Acid Ethyl ester)]-phenylacetic Acid Methyl Ester 233.8 g (1.4 mol) of 2-bromoacetic acid-ethyl ester is added to 200 g (1.204 mol) of 4-hydroxyphenylacetic acid methyl ester and 212 g (2 mol) of sodium carbonate in 2000 ml of acetone, and it is refluxed for 5 hours. The solid is filtered off and evaporated to the dry state in a vacuum. The residue is chromatographed on silica gel (mobile solvent: n-hexane/ethyl acetate=15:1).

Yield: 288.5 g (95% of theory) of a colorless oil.
Elementary analysis:

| | | |
|---|---|---|
| Cld: | C 61.90 | H 6.39 |
| Fnd: | C 61.75 | H 6.51 |

EXAMPLE 4b
2-[4-(3-oxapropionic Acid Ethyl ester)]-phenyl-2-bromoacetic Acid Methyl Ester 201 g (1.13 mol) of N-bromosuccinimide and 100 mg of dibenzyl peroxide are added to 285 g (1.13 mol) of the title compound of Example 4a, dissolved in 2000 ml of carbon tetrachloride, and it is refluxed for 8 hours. It is cooled in an ice bath, the precipitated succinimide is filtered off, and the filtrate is evaporated to the dry state in a vacuum. The residue is purified on silica gel (mobile solvent: n-hexane/acetone =15:1).

Yield: 359.2 g (96% of theory) of a colorless, viscous oil.
Elementary analysis:

| | | | |
|---|---|---|---|
| Cld: | C 47.28 | H 4.57 | Br 24.16 |
| Fnd: | C 47.19 | H 4.71 | Br 24.05 |

EXAMPLE 4c
2-[4-(3-oxapropionic Acid Ethyl Ester)]-phenyl-2-[1-(1,4,7,10-tetraazacyclododecan-7-yl]-acetic Acid Methyl Ester 350 g (1.057 mol) of the title compound of Example 4b is added to 603 g (3.5 mol) of 1,4,7,10-tetraazacyclododecane in 6000 ml of chloroform, and it is stirred overnight at room temperature. It is extracted 3 times with 3000 ml of water, the organic phase is dried on magnesium sulfate and evaporated to the dry state in a vacuum. The residue is used in the next reaction (3d) without further purification.

Yield: 448 g (quantitative) of a viscous oil.
Elementary analysis:

| | | | |
|---|---|---|---|
| Cld: | C 59.70 | H 8.11 | N 13.26 |
| Fnd: | C 59.58 | H 8.20 | N 13.18 |

EXAMPLE 4d
2-[4-(3-oxapropionic Acid)]-phenyl-2-[1,4,7-tris(Carboxymethyl)-1,4,7,10-tetraaza-cyclododecan-10-yl]-acetic Acid 445 g (1.053 mol) of the title compound of Example 4c and 496 g (5.27 mol) of chloroacetic acid are dissolved in 4000 ml of water. It is set at pH 10 with 30% aqueous sodium hydroxide solution It is heated to 70° C., and the pH is kept at 10 by adding 30% aqueous sodium hydroxide solution. It is stirred for 8 hours at 70° C. It is then set at pH 13 and refluxed for 30 minutes. The solution is cooled in an ice bath and set at a pH of 1 by adding concentrated hydrochloric acid. It is evaporated to the dry state in a vacuum. The residue is taken up in 4000 ml of methanol and absorptively precipitated for one hour at room temperature. Precipitated common salt is filtered out, the filtrate is evaporated to the dry state, and the residue is purified on silica gel RP-18 (mobile solvent: gradient that consists of water/ethanol/acetonitrile).

Yield: 403 g (69% of theory) of a colorless solid.
Water content: 10.2%
Elementary analysis (relative to anhydrous substance):

| | | | |
|---|---|---|---|
| Cld: | C 51.98 | H 6.18 | N 10.10 |
| Fnd: | C 51.80 | H 6.31 | N 10.01 |

EXAMPLE 4e

2-[4-(3-oxapropionic Acid)]-phenyl-2-[1,4,7-tris(Carboxymethyl)-1,4,7,10-tetraaza-cyclododecan-10-yl]-acetic Acid, Gd-complex 130.73 g (360.65 mmol) of gadolinium oxide is added to 400 g (721.3 mmol) of the title compound of Example 4d in 2000 ml of water, and it is stirred for 5 hours at 80° C. The solution is filtered, and the filtrate is freeze-dried.

| Yield: | 511 g (quantitative) of an amorphous solid. | | | |
|---|---|---|---|---|
| Water content: | 11.0% | | | |
| Elementary analysis (relative to anhydrous substance): | | | | |
| Cld: | C 40.67 | H 4.41 | Gd 22.19 | N 7.98 |
| Fnd: | C 40.51 | H 4.52 | Gd 22.05 | N 8.03 |

EXAMPLE 4f 2,6-N,N'-bis{2-[4-(3-oxapropionyl)-phenyl]-2-[1,4,7-tris(Carboxylatomethyl)-1,4,7,10-tetraazacyclododecan-10-yl]-acetic acid]-lysine-[4-perfluorooctylsulfonyl)-piperazine]-amide, Digadolinium Complex, disodium Salt 10 g (14.36 mmol) of the title compound of Example 3a, 3.45 g (30 mmol) of N-hydroxysuccinimide, 2.54 g (60 mmol) of lithium chloride and 21.26 g (30 mmol) of the title compound of Example 4e are dissolved in 250 ml of dimethyl sulfoxide while being heated slightly. At 10° C., 16.51 g (80 mmol) of N,N-dicyclohexylcarbodiimide is added, and it is then stirred overnight at room temperature. The solution is poured into 2000 ml of acetone and stirred for 10 minutes. The precipitated solid is filtered off and then purified by chromatography (silica gel RP-18, mobile solvent: gradient that consists of water/ethanol/acetonitrile). It is dissolved in a little water, set at pH 7.4 with sodium hydroxide solution and freeze-dried.

| Yield: | 21.02 g (69% of theory) of a colorless solid. |
|---|---|
| Water content: | 11.2% |
| Elementary analysis (relative to anhydrous substance): | |

Cld:
C 37.36  H 3.66  F 15.22  Gd 14.82  N 7.92  Na 2.17  S 1.51
Fnd:
C 37.28  H 3.74  F 15.14  Gd 14.75  N 8.03  Na 2.23  S 1.46

EXAMPLE 5a 2,6-N,N'-bis[6-carbonylmethyl-3,9-bis(t-butyloxycarbonylmethyl)-3,6,9-triazaundecane-1,11-dicarboxylic Acid-bis(t-butylester)]-lysine-[1-(4-perfluorooctylsulfonyl)-piperazine]-amide 10.32 g (50 mmol) of N,N-dicyclohexylcarbodiimide is added at 0° C. to a solution that consists of 10 g (14.36 mmol) of the title compound of Example 3a, 18.53 g (30 mmol) of 3,9-bis(t-butyloxycarbonylmethyl)-6-carboxymethyl-3,6,9-triazaundecane-1,11-dicarboxylic acid-bis(t-butylester) and 3.45 g (30 mol) of N-hexoxysuccinimide, dissolved in 150 ml of dimethylformamide. It is stirred for 3 hours at 0° C., then overnight at room temperature. Precipitated urea is filtered out, the filtrate is evaporated to the dry state in a vacuum and chromatographed on silica gel (mobile solvent: dichloromethane/ethanol=20:1).

| Yield: | 19.60 g (72% of theory) of a viscous oil. | | | |
|---|---|---|---|---|
| Elementary analysis: | | | | |
| Cld: | C 49.41 | H 6.75 | F 17.03 | N 7.39 | S 1.69 |
| Fnd: | C 49.35 | H 6.82 | F 16.92 | N 7.32 | S 1.62 |

EXAMPLE 5b 2,6-N,N-bis[6-carbonylmethyl-3,9-bis(Carboxylatomethyl)-3,6,9-triazaundecanedicarboxylic Acid-1-carboxy-11-carboxylato-lysine-[1-(4-perfluorooctylsulfonyl)-piperazine]-amide, Gd-complex, sodium salt]

15 g (7.91 mol) of the title compound of Example 5a is dissolved in 50 ml of chloroform, and 200 ml of trifluoroacetic acid is added. It is stirred for 10 minutes at room temperature. It is evaporated to the dry state in a vacuum, and the residue is dissolved in 150 ml of water. 2.87 g (7.91 mmol) of gadolinium oxide is added, and it is stirred for 5 hours at 80° C. It is allowed to cool to room temperature and set at pH 7.4 with 2N sodium hydroxide solution. The solution is evaporated to the dry state in a vacuum and purified on RP-18 (mobile solvent: gradient that consists of water/ethanol/acetonitrile).

| Yield: | 8.11 g (57% of theory) of a colorless, amorphous solid. | | | | |
|---|---|---|---|---|---|
| Water content: | 9.6% | | | | |
| Elementary analysis (relative to anhydrous substance): | | | | | |
| Cld: | C 30.70 | H 3.08 | Gd 17.48 | N 7.78 | Na 2.56 | S 1.78 |
| Fnd: | C 30.58 | H 3.19 | Gd 17.42 | N 7.71 | Na 2.68 | S 1.72 |

EXAMPLE 6a

6-N-benzyloxycarbonyl-2-N-[6-carboxymethyl-3,9-bis(t-butyloxycarbonylmethyl)-3,6,9-triazaundecane-1,11-dicarboxylic acid-bis(t-butylester)]-lysine-[1(4-perfluorooctylsulfonyl)-piperazine]-amide 8.25 g (40 mol) of N,N-dicyclohexylcarbodiimide is added at 0° C. to a solution that consists of 20 g (24.08 mmol) of the title compound of Example 1c, 14.88 g (24.08 mmol) of 3,9-[bis(t-butyloxycarbonylmethyl)-6-carboxymethyl-3,6,9-triazaundecane-1,11-dicarboxylic acid-bis(t-butylester) and 2.88 g (25 mol) of N-hydroxysuccinimide, dissolved in 100 ml of dimethylformamide. It is stirred for 3 hours at 0° C., then overnight at room temperature. Precipitated urea is filtered out, the filtrate is evaporated to the dry state in a vacuum and chromatographed on silica gel (mobile solvent: dichloromethane/ethanol=20:1).

| Yield: | 27.21 g (79% of theory) of a viscous oil. | | | | |
|---|---|---|---|---|---|
| Elementary analysis: | | | | | |
| Cld: | C 47.03 | H 5.64 | F 22.58 | N 6.85 | S 2.24 |
| Fnd: | C 46.94 | H 5.58 | F 22.65 | N 6.84 | S 2.31 |

EXAMPLE 6b

2-N-[Carbonylmethyl-3,9-bis(t-butyloxycarbonylmethyl)-3,6,9-triazaundecane-1,11-dicarboxylic Acid-bis(t-butylester)]-lysine-[1-(4-perfluorooctylsulfonyl)-piperazine]-amide 25 g (17.48 mmol) of the title compound of Example 6a is dissolved in 350 ml of ethanol, and 5 g of palladium catalyst (10% Pd/C) is added. It is hydrogenated at room temperature. Catalyst is filtered out, and the filtrate is evaporated to the dry state in a vacuum.

| Yield: | 22.66 g (quantitative) of a colorless solid. | | | | |
|---|---|---|---|---|---|
| Elementary analysis: | | | | | |
| Cld: | C 44.48 | H 5.75 | F 24.92 | N 7.56 | S 2.47 |
| Fnd: | C 44.59 | H 5.81 | F 25.03 | N 7.46 | S 2.52 |

EXAMPLE 6c

6-N-[1,4,7-tris(Carboxylatomethyl)-1,4,7,10-tetraazacyclododecane-10-(Pentanoyl-3-aza-4-oxo-5-methyl-5yl)]-2-N-[6-carbonylmethyl-3,9-bis(t-butyloxycarbonylmethyl)-3,6,9-triazaundecane-1,11-dicarboxylic Acid-bis(t-butylester)]-lysine-[1-(4-perfluorooctylsulfonyl)-piperazine-]-amide, Gd-complex 20 g (15.43 mmol) of the title compound of Example 6b, 1.78 g (15.43 mmol) of N-hydroxysuccinimde, 1.48 g (35 mmol) of lithium chloride and 9.72 g (15.43 mmol) of 1,4,7-tris(Carboxylatomethyl)-10-(3-aza-4-oxo-5-meth-5yl)-pentanoic acid-1,4,7,10-tetraazacyclododecane, Gd-complex are dissolved in 150 ml of dimethyl sulfoxide while being heated slightly. At 10° C., 5.16 g (25 mmol) of N,N-dicyclohexylcarbodiimide is added, and it is then stirred overnight at room temperature. The solution is poured into 2500 ml of acetone and stirred for 10 minutes. The precipitated solid is filtered off and then purified by chromatography (silica gel RP-18, mobile solvent: gradient that consists of water/ethanol/acetonitrile).

| Yield: | 22.94 g (78% of theory) of a colorless solid. | | | | |
|---|---|---|---|---|---|
| Water content: | 7.9% | | | | |
| Elementary analysis | | | | | |
| (relative to anhydrous substance): | | | | | |
| Cld: | C 42.22 | H 5.29 | F 16.95 | Gd 8.25 | N 8.82 | S 1.68 |
| Fnd: | C 42.15 | H 5.41 | F 16.87 | Gd 8.13 | N 8.70 | S 1.60 |

EXAMPLE 6d

6-N-[1,4,7-tris(Carboxylatomethyl)-1,4,7,10-tetraazacyclododecane-10-(3-aza-4-oxo-5-methyl-5-yl)-pentanoyl)]-2-N-[6-carbonylmethyl-3,9-bis(Carboxylatomethyl)-3,6,9-triazaundecanedicarboxylic Acid-carboxy-11-carboxylato-2]-lysine-[1-(4-perfluorooctylsulfonyl)-piperazine]-amide, Digadolinium Complex, Sodium Salt 20 g (10.49 mmol) of the title compound of Example 6c is dissolved in 200 ml of trifluoroacetic acid. It is stirred for 60 minutes at room temperature. It is evaporated to the dry state in a vacuum, and the residue is dissolved in 150 ml of water. 1.90 g (5.25 mmol) of gadolinium oxide is added, and it is stirred for 5 hours at 80° C. It is allowed to cool to room temperature and set at pH 7.4 with sodium hydroxide solution. The solution is evaporated to the dry state in a vacuum and purified on silica gel RP-18 (mobile solvent: gradient that consists of water/ethanol/acetonitrile).

| Yield: | 11.89 g (61% of theory) of a colorless, amorphous solid. | | | | | |
|---|---|---|---|---|---|---|
| Water content: | 10.2% | | | | | |
| Elementary analysis | | | | | | |
| (relative to anhydrous substance): | | | | | | |
| Cld: | | | | | | |
| C 32.97 | H 3.47 | F 17.39 | Gd 16.93 | N 9.05 | Na 1.24 | S 1.73 |
| Fnd: | | | | | | |
| C 32.90 | H 3.53 | F 17.31 | Gd 16.87 | N 8.92 | Na 1.33 | S 1.67 |

EXAMPLE 7a 5,6-bis(Benzoyloxy)-3oxa-hexanoic Acid-t-butyl Ester 100 g (376.2 mmol) of 1,2-di-O-benzyl-glycerine [produced according to Chem. Phys. Lipids (1987), 43(2), 113–27] and 5 g of tetrabutylammonium hydrogen sulfate are dissolved in a mixture that consists of 400 ml of toluene and 200 ml of 50% aqueous sodium hydroxide solution. At 0° C., 78 g (400 mmol) of 2-bromoacetic acid-t-butylester is added in drops over 30 minutes, and it is then stirred for 3 hours at 0° C. The organic phase is separated, dried on magnesium sulfate and evaporated to the dry state in a vacuum. The residue is chromatographed on silica gel (mobile solvent: n-hexane/acetone=20:1).

| Yield: | 133.4 g (94% of theory) of a colorless oil. | |
|---|---|---|
| Elementary analysis: | | |
| Cld: | C 71.48 | H 7.82 |
| Fnd: | C 71.61 | H 7.92 |

EXAMPLE 7b 5,6-bis(Benzyloxy)-3-oxa-hexanoic Acid 130 g (336.4 mmol) of the title compound of Example 7a is dissolved in 200 ml of dichloromethane, and 100 ml of trifluoroacetic acid is added at 0° C. It is stirred for 4 hours at room temperature and then evaporated to the dry state. The residue is crystallized from pentane/diethyl ether.

| Yield: | 102.2 g (92% of theory) of a waxy solid | |
|---|---|---|
| Elementary analysis: | | |
| Cld: | C 69.07 | H 6.71 |
| Fnd: | C 69.19 | H 6.32 |

EXAMPLE 7c

6-N-benzyloxycarbonyl-2-N-[1,4,7-tris(Carboxylatomethyl)1,4,7,10-tetraazacyclododecane-10-(Pentanoyl-3-aza-4-oxo-5-methyl-5-yl)]-lysine-[1-(4-perfluorooctylsulfonyl)-piperazine]-amide, Gd-complex 50 g (60.20 mmol) of the title compound of Example 1c, 6.93 g (60.20 mmol) of N-hydroxysuccinimide, 5.09 g (120 mmol) of lithium chloride and 37.91 g (60.20 mmol) of 1,4,7-tris(Carboxylatomethyl)-1,4,7,10-tetraazacyclododecane-10-pentanoyl-3-aza-4-oxo-5-methyl-5yl), Gd-complex are dissolved in 400 ml of dimethyl sulfoxide while being heated slightly. At 10° C., 20.63 g (100 mmol) of N,N-dicyclohexylcarbodiimide is added, and it is then stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 75.53 g (87% of theory) of a colorless solid.
Water content: 10.1%
Elementary analysis
(relative to anhydrous substance):

| Cld: | C 37.48 | H 3.84 | F 22.39 | Gd 10.90 | N 8.74 | S 2.22 |
|---|---|---|---|---|---|---|
| Fnd: | C 37.39 | H 4.02 | F 22.29 | Gd 10.75 | N 8.70 | S 2.22 |

EXAMPLE 7d

2-N-[1,4,7-tris(Carboxylatomethyl)-1,4,7,10-tetraazacyclododecane-10-(Pentanoyl-3aza-4-oxo-5methyl-5yl]-lysine-[1-(4-perfluorooctylsulfonyl)-piperazine]-amide, Gd Complex 70 g (48.53 mmol) of the title compound of Example 7c is dissolved in 500 ml of water/100 ml of ethanol, and 5 g of palladium catalyst (10% Pd/C) is added. It is hydrogenated at room temperature. Catalyst is filtered out, and the filtrate is evaporated to the dry state in a vacuum.

Yield: 63.5 g (quantitative) of a colorless solid.
Water content: 9.8%
Elementary analysis
(relative to anhydrous substance):

| Cld: | C 37.48 | H 3.84 | F 22.39 | Gd 10.90 | N 8.74 | S 2.22 |
|---|---|---|---|---|---|---|
| Fnd: | C 37.39 | H 4.03 | F 22.31 | Gd 10.78 | N 8.65 | S 2.20 |

EXAMPLE 7e

6-N-[5,6-bis(Benzyloxy)-3-oxahexanoyl]-2-N-[1,4,7-tris(Carboylatomethyl)-1,4,7,10-tetraazacyclododecane-10-(Pentanoyl-3-aza-4-oxo-5-methyl-5yl)]-lysine-[1-(4-perfluorooctylsulfonyl)-piperazine]-amide, Gd-complex 10 g (7.64 mmol) of the title compound of Example 7d, 3.30 g (10 mmol) of the title compound of Example 7b, 0.85 g (20 mmol) of lithium chloride and 1.15 g (10 mmol) of N-hydroxysuccinimide are dissolved in 150 ml of dimethyl sulfoxide while being heated slightly. At 10° C., 3.10 g (15 mmol) of N,N'-dicyclohexylcarbodiimide is added, and it is stirred for 8 hours at room temperature. The reaction solution is poured into 2000 ml of acetone, and the deposited precipitate is isolated. The is purified on silica gel RP-18 (mobile solvent: gradient that consists of water/ethanol/acetonitrile).

Yield: 11.14 g (90% of theory) of a colorless, amorphous solid.
Water content: 4.3%
Elementary analysis
(relative to anhydrous substance):

| Cld: | C 41.51 | H 4.29 | F 19.93 | N 7.78 | Gd 9.70 | S 1.98 |
|---|---|---|---|---|---|---|
| Fnd: | C 41.45 | H 4.38 | F 19.84 | N 7.70 | Gd 9.58 | S 1.90 |

EXAMPLE 7f

6-N-(5,6-dihydroxy-3-oxahexanoyl)-2-N-[1,4,7-tris-carboxylatomethyl)-1,4,7,10-tetraazacyclododecane-10-pentanoyl-3-aza-4-oxo-5-methyl-5-yl)]-lysine [1-(4-perfluorooctylsulfonyl)-piperazine]-amide, Gd-complex 10 g (6.17 mmol) of the title compound of Example 7e is dissolved in 200 ml of ethanol, and 3 g of palladium-catalyst (10% Pd/C) is added. It is hydrogenated at room temperature. Catalyst is filtered out, and the filtrate is evaporated to the dry state in a vacuum.

Yield: 8.89 g (quantitative) of a colorless solid.
Water content: 3.1%
Elementary analysis
(relative to anhydrous substance):

| Cld: | C 35.03 | H 3.99 | F 22.42 | Gd 10.92 | N 8.75 | S 2.23 |
|---|---|---|---|---|---|---|
| Fnd: | C 34.95 | H 4.12 | F 22.30 | Gd 10.78 | N 8.71 | S 2.18 |

EXAMPLE 8a

6-N-benzyloxycarbonyl-2-N[-5,6-bis(Benzyloxy)-3-oxa-hexanoyl]-lysine-[1-(4-perfluorooctylsulfonyl)-piperazine]-amide 9.28 g (45 mmol) of N,N-dicyclohexylcarbodiimide is added at 0° C. to a solution that consists of 20 g (24.08 mmol) of the title compound of Example 1c, 9.91 g (30 mmol) of the title compound of Example 7b and 3.45 g (30 mmol) of N-hydroxysuccinimide, dissolved in 100 ml of dimethylformamide. It is stirred for 3 hours at 0° C., then overnight at room temperature. Precipitated urea is filtered out, the filtrate is evaporated to the dry state in a vacuum, and it is chromatographed on silica gel (mobile solvent: dichloromethane/ethanol=20:1).

Yield: 24.50 g (89% of theory) of a viscous oil.
Elementary analysis:

| Cld: | C 47.29 | H 4.14 | F 28.26 | N 4.90 | S 2.81 |
|---|---|---|---|---|---|
| Fnd: | C 47.14 | H 4.26 | F 28.17 | N 4.91 | S 2.69 |

EXAMPLE 8b

2-N-(5,6-dihydroxy-3-oxahexanoyl)-lysine-[1-(4-perfluorooctylsulfonyl)-piperazine]-amide 20 g (17.5 mmol) of the title compound of Example 8a is dissolved in 300 ml of ethanol, and 5 g of palladium-catalyst (10% Pd/C) is added. It is hydrogenated at room temperature. Catalyst is filtered out, and the filtrate is evaporated to the dry state in a vacuum.

Yield: 17.65 g (quantitative) of a colorless solid.
Elementary analysis:

| Cld: | C 44.05 | H 4.10 | F 32.02 | N 5.55 | S 3.18 |
|---|---|---|---|---|---|
| Fnd: | C 43.96 | H 4.21 | F 31.94 | N 5.48 | S 3.24 |

EXAMPLE 8c

6-N-[1,4,7-tris(Carboxylatomethyl)-1,4,7,10-tetraazacyclododecane-10-(Pentanoyl-3-aza-4-oxo-5-methyl-5yl)]-lysine-[1-(4-perfluorooctylsulfonyl)-piperazine]-amide, Gd-complex 15 g (14.87 mmol) of the title compound of Example 8b, 1.73 g (15 mmol) of N-hydroxy-succinimide, 1.27 g (30 mmol) of lithium chloride and 9.48 g (15 mmol) of 1,4,7-tris(Carboxylatomethyl)-10-(3-aza-4-oxo-5-methyl-5-yl)-pentanoic acid-1,4,7,10-tetraazacyclododecane, Gd-complex, are dissolved in 100 ml of dimethyl sulfoxide while being heated slightly. At 10° C., 5.16 g (25 mol) of N,N-dicyclohexylcarbodiimide is added, and it is then stirred overnight at room temperature. The solution is poured into 1500 ml of acetone and stirred for 10 minutes. The precipitated solid is filtered off and then purified by chromatography (silica gel RP-18 mobile solvent: gradient that consists of water/ethanol/acetonitrile).

Yield: 19.28 g (80% of theory) of a colorless solid.
Water content: 10.3%
Elementary analysis
(relative to anhydrous substance):

| Cld: | C 41.51 | H 4.29 | F 19.93 | Gd 9.70 | N 7.78 | S 1.98 |
|---|---|---|---|---|---|---|
| Fnd: | C 41.37 | H 4.40 | F 19.88 | Gd 9.58 | N 7.67 | S 1.85 |

EXAMPLE 9a
6-N-benzyloxycarbonyl-2-N-[2,6-N,N'-bis(Benzyloxycarbonyl)-lysyl]-lysine-[1-(4-perfluorooctylsulfonyl)-piperazine]-amide 20 g (24.08 mmol) of the title compound of Example 1c and 2.53 g (25 mmol) of triethylamine are dissolved in 200 ml of tetrahydrofuran (THF), and 14.46 g (27 mmol) of di-N,N'-Z-lysine paranitrophenol ester is added. It is stirred for 5 hours at 50° C. It is evaporated to the dry state in a vacuum, and the residue is chromatographed on silica gel.

Mobile solvent: dichloromethane/methanol = 20:1).
Yield: 28.07 g (95% of theory) of a colorless solid.
Elementary analysis:

| Cld: | C 46.99 | H 4.19 | F 26.32 | N 6.85 | S 2.61 |
|---|---|---|---|---|---|
| Fnd: | C 47.08 | H 4.32 | F 26.21 | N 6.75 | S 2.54 |

EXAMPLE 9b
2-N-(Lysyl)-lysine-[1-(4-perfluorooctylsulfonyl)-piperazine]-amide, trihydrobromide 100 ml of hydrobromic acid in glacial acetic acid (48%) is added to 25 g (20.37 mmol) of the title compound of Example 9a, and it is stirred for 2 hours at 40° C. It is cooled to 0° C., 1500 ml of diethyl ester is added in drops, and the precipitated solid is filtered off. After drying in a vacuum (60° C.), 21.52 g (99% of theory) of a slightly yellow-colored, crystalline solid is obtained.

Elementary analysis:

| Cld: | C 27.01 | H 3.40 | Br 22.46 | F 30.26 | N 7.87 | S 3.00 |
|---|---|---|---|---|---|---|
| Fnd: | C 26.92 | H 3.53 | Br 22.15 | F 30.14 | N 7.69 | S 2.87 |

EXAMPLE 9c
6-N-[1,4,7-tris(Carboxylatomethyl)-1,4,7,10-tetraazacyclododecane-10-(Pentanoyl-3-aza-4-oxo-5-methyl-5yl)]-2-N-[2,6-N,N'-bis[1,4,7-tris carboxylatomethyl)-1,4,7,10-tetraazacyclododecane-10-(Pentanoyl-3-aza-4-oxo-5-methyl-5-yl)]-lysyl]-lysine-[1-(4-perfluorooctylsulfonyl)-piperazine]-amide, trigadolinium Complex 31.49 g (50 mmol) of 1,4,7-tris(Carboxylatomethyl)-10-(3-aza-4-oxo-5-methyl-5-yl)-pentanoic Acid, Gd-complex 6.91 g (60 mmol) of N-hydroxysuccinimide and 4.24 g (100 mmol) of lithium chloride are dissolved in 350 ml of dimethyl sulfoxide while being heated slightly. At 10° C., 16.51 g (80 mmol) of N,N-dicyclohexylcarbodiimide is added, and it is stirred for 5 hours at 10° C. 10 g (9.37 mmol) of the title compound of Example 9b and 3.03 g (30 mmol) of triethylamine are added to this mixture, and it is stirred for 12 hours at 60° C. It is allowed to cool to room temperature, and the mixture is poured into 3000 ml of acetone. The deposited precipitate is filtered off, purified on silica gel RP-18 (mobile solvent: gradient that consists of water/ethanol/acetonitrile).

Yield: 16.7 g (67% of theory) of a colorless solid.
Water content: 7.9%
Elementary analysis
(relative to anhydrous substance):

| Cld: | C 36.58 | H 4.43 | F 12.14 | Gd 17.74 | N 11.06 | S 1.14 |
|---|---|---|---|---|---|---|
| Fnd: | C 36.47 | H 4.54 | F 12.03 | Gd 17.65 | N 10.95 | S 1.21 |

EXAMPLE 10a
1,7-bis(Benzyloxycarbonyl)-4-(3,6,9,12,15-pentaoxahexadecanoyl)-1,4,7,10-tetraazacyclododecane 24.73 g (100 mmol) of EEDQ (2-ethoxy-1,2-dihydroquinoline-1-carboxylic ether ester) is added at 0° C. to 18.13 g (68.1 mmol) of 3,6,9,12,15-pentaoxahexadecanoic acid and 30 g (68.1 mmol) of 1,7-di-Z-cyclene produced according to Z. Kovacs and A. D. Sherry, J. Chem. Soc. Chem. Commun. (1995), 2, 185, in 300 ml of tetrahydrofuran, and it is stirred overnight at room temperature. It is evaporated to the dry state in a vacuum and chromatographed on silica gel (mobile solvent: dichloromethane/methanol =20:1).

Yield: 19.13 g (42% of theory) of a colorless solid.
Elementary analysis:

| Cld: | C 61.03 | H 7.61 | N 8.13 |
|---|---|---|---|
| Fnd: | C 60.92 | H 7.75 | N 8.04 |

EXAMPLE 10b
1,7-bis(Benzyloxycarbonyl)-4-(3,6,9,12,15-pentaoxahexadecanoyl)-10-(2H,2H,4H,5H,5H-3-oxa-perfluorotridecanoyl)-1,4,7,10-tetraazacyclododecane 12.36 g (50 mmol) of EEDQ (2-ethoxy-1,2-dihydroquinoline-1-carboxylic acid ethyl ester) is added at 0° C. to 18 g (26.91 mmol) of the title compound of Example 10a and 14.05 g (26.91 mmol) of 2H,2H,4H,4H,5H,5H-3-oxa-perfluorotridecanoic acid, produced according to DE 19603033, in 300 ml of tetrahydrofuran, and it is stirred overnight at room temperature. It is evaporated to the dry state in a vacuum and chromatographed on silica gel (mobile solvent: dichloromethane/methanol=20:1).

Yield: 21.51 g (67% of theory) of a colorless solid
Elementary analysis:

| Cld: | C 47.32 | H 4.82 | F 27.07 | N 4.70 |
|---|---|---|---|---|
| Fnd: | C 47.26 | H 5.01 | F 26.94 | N 4.59 |

EXAMPLE 10c
1-(3,6,9,12,15-pentaoxahexadecanoyl)-7-(2H,2H,4H,4H,5H,5H-3-oxaperfluorotridecanoyl)-1,4,7,10-tetraazacyclododecane 20 g (16.77 mmol) of the title compound of Example 1d is dissolved in 200 ml of ethanol, and 2.5 g of palladium catalyst (10% Pd/C) is added. It is hydrogenated at room temperature. Catalyst is filtered out, and the filtrate is evaporated to the dry state in a vacuum.

Yield: 15.5 g (quantitative) of a colorless solid.
Elementary analysis:

| Cld: | C 40.27 | H 4.90 | F 34.93 | N 6.06 |
|---|---|---|---|---|
| Fnd: | C 40.15 | H 4.99 | F 34.87 | N 5.94 |

EXAMPLE 10d
1,7-bis(1,4,7-tris(Carboxylatomethyl)-1,4,7,10-tetraazacyclododecane-10-(Pentanoyl-3-aza-4-oxo-5-methyl-5-yl)]-4-(3,6,9,12,15-pentaoxahexadecanoyl)-10-(2H,2H,4H,4H,5H,5H-3-oxaperfluorotridecanoyl)-1,4,7,10-tetraazacyclododecane, Gd-complex 15 g (16.22 mmol) of the title compound of Example 10c, 4.60 g (40 mmol) of N-hydroxysuccinimide, 3.39 g (80 mmol) of lithium chloride and 25.19 g (40 mmol) of 1,4,7-tris-(Carboxylatomethyl)-10-(3-aza-4-oxo-5-methyl-5yl)Pentanoic Acid, Gd-complex, are dissolved in 300 ml of dimethyl sulfoxide while being heated slightly. At 10° C., 24.73 g (100 mmol) of EEDQ is added, and it is then stirred overnight at room temperature. The solution is poured into 3000 ml of acetone and stirred for 10 minutes.

The precipitated solid is filtered off and then purified by chromatography (silica gel RP-18) (mobile solvent: gradient that consists of water/ethanol/acetonitrile).

Yield: 19.86 g (57% of theory) of a colorless solid
Water content: 11.3%
Elementary analysis
(relative to anhydrous substance):

| Cld: | C 38.58 | H 4.74 | F 15.04 | Gd 14.64 | N 9.13 |
|---|---|---|---|---|---|
| Fnd: | C 38.47 | H 4.91 | F 14.95 | Gd 14.57 | N 9.04 |

EXAMPLE 11a
3,5-dinitrobenzoic Acid-1-[(4-perfluorooctylsulfonyl)-piperazine]-amide A solution of 8.76 g (38 mmol) of 3,5-dinitrobenzoyl chloride in 55 ml of dichloromethane is added in drops at 0° C. to 20 g (35.2 mmol) of perfluorooctylsulfonylpiperazine and 8.1 g (80 mmol) of triethylamine, dissolved in 200 ml of dichloromethane, and it is stirred for 3 hours at 0° C. 200 ml of 5% aqueous hydrochloric acid is added, and it is stirred for 5 minutes at room temperature. The organic phase is separated, dried on magnesium sulfate and evaporated to the dry state in a vacuum. The residue is chromatographed on silica gel (mobile solvent: dichloromethane/acetone=15:1).

Yield: 24.96 g (93% of theory) of a colorless solid.
Elementary analysis:

| Cld: | C 29.35 | H 1.45 | F 42.37 | N 7.35 | S 4.21 |
|---|---|---|---|---|---|
| Fnd: | C 29.28 | H 1.61 | F 42.15 | N 7.25 | S 4.15 |

EXAMPLE 11b
3,5-diaminobenzoic Acid-[1-(4-perfluorooctylsulfonyl)-piperazine]-amide 20 g (26.23 mmol) of the title compound of Example 11a is dissolved in 400 ml of ethanol, and 6 g of palladium catalyst (10% Pd/C) is added. It is hydrogenated at room temperature. Catalyst is filtered out, and the filtrate is evaporated to the dry state in a vacuum.

Yield: 18.43 g (quantitative) of a cream-colored solid.
Elementary analysis:

| Cld: | C 32.49 | H 2.15 | F 45.98 | N 7.98 | S 4.57 |
|---|---|---|---|---|---|
| Fnd: | C 32.29 | H 2.35 | F 45.69 | N 7.81 | S 4.40 |

EXAMPLE 11c
3,5-N,N'-bis[1,4,7-tris(Carboxylatomethyl)-1,4,7,10-tetraazacyclododecane-10-(Pentanoyl-3-aza-4-oxo-5-methyl-5-yl-)]-benzoic Acid-[1-(4-perfluorooctyl-sulfonyl)-piperazine]-amide, Gd-complex 10 g (14.24 mmol) of the title compound of Example 11b, 3.45 g (30 mmol) of N-hydroxysuccinimide, 2.54 g (60 mmol) of lithium chloride and 18.89 g (30 mmol) of 1,4,7-tris-(Carboxylatomethyl)-10-(3-aza-4-oxo-5-methyl-5yl)-pentanoic acid, Gd-complex are dissolved in 200 ml of dimethyl sulfoxide while being heated slightly. At 10° C., 10.32 g (50 mmol) of N,N-dicyclohexylcarbodiimide is added, and it is then stirred overnight at room temperature. The solution is poured into 2000 ml of acetone and stirred for 10 minutes. The precipitated solid is filtered off and then purified by chromatography (silica gel RP-18, mobile solvent: gradient that consists of water/ethanol/acetonitrile).

Yield: 19.74 g (72% of theory) of a colorless solid.
Water content: 11.8%
Elementary analysis
(relative to anhydrous substance):

| Cld: | C 35.55 | H 3.72 | F 16.77 | Gd 16.33 | N 10.18 | S 1.67 |
|---|---|---|---|---|---|---|
| Fnd: | C 35.48 | H 3.84 | F 16.58 | Gd 16.24 | N 10.07 | S 1.58 |

EXAMPLE 12
a) 3-oxa-2H,2H,4H,4H,5H,5H-perfluorotridecanecarboxylic Acid-t-butyl ester 25.0 g (53.8 mmol) of 1H,1H,2H,2H-perfluoro-1-decanol [commercially available from the Lancaster Company] is dissolved in 250 ml of absolute toluene and mixed at room temperature with a catalytic amount (about 0.75 g) of tetra-n-butyl-ammonium hydrogen sulfate. Then, a total of 7.55 g (134.6 mmol; 2.5 equivalents relative to the alcohol component used) of fine-powder potassium hydroxide powder is added at 0° C., followed by 15.73 g (80.7 mmol, 1.5 equivalents relative to the alcohol component used) of bromoacetic acid-tert-butyl ester, and it is allowed to stir for 2 more hours at 0° C. The reaction solution thus obtained is stirred for 12 more hours at room temperature and is mixed with a total of 500 ml of ethyl acetate and 250 ml of water for the purposes of working-up. The organic phase is separated and washed twice with water. After the organic phase has dried on sodium sulfate, salt is suctioned out, and the solvent is drawn off in a vacuum. The remaining oily residue is purified as an eluant on silica gel with use of ethyl acetate/hexane (1:10) as an eluant.

| Yield: 26.3 g (84.6% of theory) of the above-mentioned title compound as a colorless and strongly viscous oil. Elementary analysis: | | | |
|---|---|---|---|
| Cld: | C 33.23 | H 2.61 | F 55.85 |
| Fnd: | C 33.29 | H 2.61 | F 55.90 | b) 3-oxa-2H,2H,4H,4H,5H,5H-perfluorotridecanecarboxylic Acid 20.0 g (34.58 mmol) of the title compound of Example 12a) is suspended in 200 ml of a mixture, consisting of methanol and 0.5 molar sodium hydroxide solution in a ratio of 2:1 while being stirred at room temperature, and then it is heated to 60° C. After a reaction time of 12 hours at 60° C., the now clear reaction mixture is neutralized for working-up by mixing with Amberlite$^{(R)}$ IR 120 (H$^-$ form)-cation exchanger resin, exchanger is suctioned out, and the thus obtained methanolic-aqueous filtrate is drawn off in a vacuum until a dry state is reached. The obtained amorphous-oily residue is purified as eluant on silica gel with use of ethyl acetate/n-hexane (1:3).

| Yield: 16.0 g (88.6% of theory) of the above-mentioned title compound as colorless and strongly viscous oil. Elementary analysis: | | | |
|---|---|---|---|
| Cld: | C 27.60 | H 1.35 | F 61.85 |
| Fnd: | C 27.58 | H 1.36 | F 61.90 | c) 1,7-bis{[1,4,7-tris(Carboxylatomethyl)-10-(3-aza-4-oxo-5-methyl-5-yl-pentanoyl)]-1,4,7,10-tetraazacyclododecane}-diethylenetriamine, Digadolinium-complex 2.48 g [(3.94 mmol); 2.05 molar equivalents relative to the diethylene triamine used] of the Gd-complex that is described in the Patent Application DE 197 28 954 Cl under Example 31h), 10-(4-carboxy-1-methyl-2-oxo-3-aza-butyl)-1,4,7,10-tetraazacyclododecane-1,4,7-triacetic acid and 167 mg of anhydrous lithium chloride (3.94 mmol) are dissolved at 40° C. in 40 ml of absolute dimethyl sulfoxide while being stirred, and mixed with a total of 453 mg (3.94 mmol) of N-hydroxysuccinimide at this temperature. After cooling to room temperature, the thus obtained reaction solution is mixed with 814 mg (3.946 mmol) of N,N'-dicyclohexylcarbodiimide and stirred for 2 hours at room temperature. The suspension of active ester that is obtained is then mixed with 198.3 mg (1.92 mmol) of diethylenetriamine, dissolved in 5 ml of absolute dimethyl sulfoxide, mixed and stirred for 12 hours at room temperature. For the purpose of working-up, the reaction mixture is mixed with sufficient acetone until complete precipitation of the above-mentioned title compound is achieved, the precipitate is suctioned off, dried, taken up in water, insoluble dicyclohexyl urea is filtered out, and the filtrate is desalinated on an AMICON$^{(R)}$ YM-3 ultrafiltration membrane (cut-off 3000 Da), and low-molecule components are removed. The retentate is then freeze-dried.

| Yield: 1.85 g (72.7% of theory) as a colorless lyophylizate. H$_2$O content (Karl-Fischer): 3.89% Elementary analysis (relative to anhydrous substance): | | | | |
|---|---|---|---|---|
| Cld: | C 38.03 | H 5.24 | N 13.73 | Gd 23.71 |
| End: | C 37.98 | H 5.20 | N 13.69 | Gd 23.78 | d) 1,7-bis{[1,4,7-tris(Carboxylatomethyl)-10-(3-aza-4-oxo-5-methyl-5-yl-pentanoyl)]-1,4,7,10-tetraazacyclododecane}-4-(3-oxa-2H,2H,4H,4H,5H,5H-perfluorotridecanoyl)-diethylenetriamine, Digadolinium Complex 1.27 g (2.44 mmol) of the title compound of Example 12b), dissolved in a mixture of 15 ml of tetrahydrofuran and 15 ml of dimethyl sulfoxide, are added drop by drop to a solution of 3.23 9 (2.44 mmol) of the title compound of Example 12c), in a mixture that consists of 30 ml of dimethyl sulfoxide and 3 ml of tetrahydrofuran, at 50° C. and under nitrogen atmosphere. Then, a total of 1.80 g (3.66 mmol) of EEDQ [2-ethoxy-1-ethoxycarbonyl-1,2-dihydroquinoline) is added in portions at 0° C. and allowed to stir overnight at room temperature. The reaction solution that is obtained is then mixed with sufficient acetone until the precipitation of the above-mentioned title compound is completed, the precipitate is suctioned off, dried, taken up in water, insoluble components are filtered out, and the filtrate is ultrafiltered on an AMICON$^{(R)}$ YM-3 ultrafiltration membrane (cut-off, 3000 Da), which is used both for complete desalination and for purification of the title compound of low-molecular components. The retentate is then freeze-dried.

| Yield: | 3.54 g (79.4% of theory) as a colorless lyophilizate. | | | |
|---|---|---|---|---|
| H$_2$O-content (Karl-Fischer): | 5.87%. | | | |
| Elementary analysis (relative to anhydrous substance): | | | | |
| Cld: | C 35.43 | H 4.07 | N 9.95 | F 17.64 | Gd 17.18 |
| Fnd: | C 35.42 | H 4.01 | N 9.89 | F 17.67 | Gd 17.18 |

EXAMPLE 13 a) 2-N-trifluoroacetyl-6-N-benzocarbonyl-L-lysine 100.0 g (356.7 mmol) of 6-N-benzoxylcarbonyl-L-lysine is dissolved in a mixture that consists of 1000 ml of trifluoroacetic acid and 500 ml of ethanol, and it is stirred for 24 hours at room temperature. It is evaporated to the dry state, and the residue is crystallized from diisopropyl ether.

| Yield: 128.9 g (96% of theory) of a colorless, crystalline powder. Melting point: 98.5° C. Elementary analysis: | | | |
|---|---|---|---|
| Cld: | C 51.07 | H 5.09 | N 7.44 | F 15.14 |
| Fnd: | C 51.25 | H 5.18 | N 7.58 | F 15.03 | b) 2-N-trifluoroacetyl-6-N-benzyloxycarbonyl-L-lysine[1-(4-perfluorooctylsulfonyl)-piperazine]-amide 164.2 g (0.664 mmol) of EEDQ (2-ethoxy-1,2-dihydroquinoline-1-carboxylic acid ethyl ester) is added at 0° C. to 125.0 g (332.0 mmol) of the title compound of Example 1a) and 188.7 g (332.0 mmol) of 1-perfluoroctylsulfonylpiperazine (produced according to DE 19603033) in 750 ml of tetrahydrofuran, and it is stirred overnight at room temperature. It is evaporated to the dry state in a vacuum and chromatographed on silica gel (mobile solvent: dichloromethane/methanol=20:1).

Yield: 286.0 g (93% of theory) of a colorless solid.
Melting point: 92° C.
Elementary analysis:

| Cld: | C 36.30 | H 2.83 | N 6.05 | F 41.01 | S 3.46 |
|---|---|---|---|---|---|
| Fnd: | C 36.18 | H 2.94 | N 5.98 | F 40.87 | S 3.40 | c) 6-N-benzyloxycarbonyl-L-lysine-[1-(4-perfluorooctylsulfonyl)-piperazine]-amide Ammonia gas is introduced at 0° C. for one hour into a solution that consists of 280.0 g (302.2 mol) of the title compound of Example 1b in 2000 ml of ethanol. It is then stirred for 4 hours at 0° C. It is evaporated to the dry state, and the residue is absorptively precipitated from water. The solid is filtered off and dried in a vacuum at 50° C.

Yield: 243.5 g (97.0% of theory) of an amorphous solid.
Elementary analysis:

| Cld: | C 37.60 | H 3.28 | N 6.75 | F 38.89 | S 3.86 |
|---|---|---|---|---|---|
| Fnd: | C 37.55 | H 3.33 | N 6.68 | F 38.78 | S 3.81 | d) L-lysine-[1-(4-perfluorooctylsulfonyl)-piperazine]-amide

In 1000 ml of ethanol, 200.0 g (240.8 mmol) of the compound produced under 13c) is dissolved, mixed with 5.0 g of Pearlman's catalyst (Pd 20%, C) and hydrogenated at room temperature under a hydrogen atmosphere (1 atm) until no more hydrogen uptake can be observed. Catalyst is suctioned out, thoroughly rewashed with ethanol (three times, with about 100 ml in each case) and evaporated to the dry state in a vacuum. The title compound is obtained as a strongly viscous and yellow-colored oil.

Yield: 162.5 g (96.9% of theory)
Elementary analysis:

| Cld: | C 31.04 | H 3.04 | N 3.05 | F 46.38 | S 4.60 |
|---|---|---|---|---|---|
| End: | C 31.11 | H 3.09 | N 8.08 | F 46.33 | S 4.62 | e) 6N-2N-bis-[4-[2,3-bis-(N,N-bis(t-butyloxycarbonylmethyl)-amino)-propyl]-phenyl]-3-oxa-propionyl-L-lysine-[1-(4-perfluorooctylsulfonyl)-piperazine]-amide 5.25 g (7.72 mmol) of the 4-[2,3-bis-(N,N-bis(t-butyloxycarbonylmethyl)-amino)-propyl]-phenyl}-3-oxa-propionic acid and 781.0 mg (7.72 mmol) of triethylamine are dissolved in 50 ml of methylene chloride. At −15° C., a solution that consists of 1.16 g (8.5 mmol) of isobutyl chloroformate is added in drops in 10 ml of methylene chloride within 5 minutes, and it is stirred for another 20 minutes at −15° C. Then, the solution is cooled to −25° C., and a solution that consists of 2.68 g (3.86 mmol) of the title compound of Example 13d) and 2.12 g (21.0 mmol) of triethylamine, in 70 ml of tetrahydrofuran, is added in drops within 30 minutes and stirred subsequently for 30 minutes at −15° C., and then stirring is continued overnight at room temperature. For working-up, the solvent is taken up in a vacuum, and the remaining oily residue is taken up in 250 ml of chloroform. The chloroform phase is extracted twice with 100 ml each of a 10 k aqueous ammonium chloride solution, the organic phase is dried on magnesium sulfate and evaporated to the dry state in a vacuum. The residue is chromatographed on silica gel (mobile solvent: methylene chloride/ethanol=20:1).

Yield: 5.37 g (68.8% of theory) of a colorless and very viscous oil.
Elementary analysis:

| Cld: | C 52.27 | H 6.43 | N 5.54 | F 15.97 | S 1.59 |
|---|---|---|---|---|---|
| Fnd: | C 52.22 | H 6.51 | N 5.49 | F 15.99 | S 1.63 | f) 6N-2N-bis-{4-[2,3-bis-(N,N-bis(Carboxylatomethyl)-amino)-propyl]-phenyl}-3-oxa-propionyl-L-lysine-[1-(4-perfluorooctylsulfonyl)-piperazine]-amide, Octa-sodium Salt 5.0 g (2.47 mmol) of the title compound of Example 13e) is dissolved in 60 ml of absolute dichloromethane. Then, it is mixed drop by drop at 0° C. with a total of 75 ml of trifluoroacetic acid. After a reaction time of 12 hours at room temperature, it is evaporated to the dry state in a vacuum. The remaining residue is mixed with 100 ml of water and again drawn off in a vacuum until the material is dry. The thus obtained residue is dissolved in 200 ml of distilled water, and the aqueous product solution of the above-mentioned title compound is extracted twice with 60 ml of diethyl ether in each case. The resulting aqueous product solution is made up by mixing with water to a total volume of 300 ml, insoluble components are filtered off, and the filtrate is ultrafiltered on an AMICON(R) YM-3 ultrafiltration membrane (cut-off 3000 Da), which is used both for complete desalination and for purification of the title compound of low-molecular components. The retentate is made up to a total volume of 200 ml by mixing with water, and the pH of this solution is then set at 10.0 with 15% sodium hydroxide solution. The basic, aqueous product solution is subsequently freeze-dried.

4.0 g (92.8% of theory) of the title compound is obtained in the form of the octa-sodium salt as an amorphous lyophilizate.

Water content: 5.37%
Elementary analysis
(relative to anhydrous substance):

| Cld: | C 38.46 | H 3.28 | N 6.41 | F 18.47 | S 1.83 | Na 10.52 |
|---|---|---|---|---|---|---|
| Fnd: | C 38.42 | H 3.31 | N 6.39 | F 18.51 | S 1.87 | Na 10.38 | g) 6N-2N-bis-{4-[2,3-bis-(N,N-bis(Carboxymethyl)-amino)-propyl]-phenyl}-3-oxa-propionyl-L-lysine-[1-(4-perfluorooctylsulfonyl)-piperazine]-amide, Di-manganese Complex, Tetrasodium Salt 1.94 g (1.11 mmol) of the title compound of Example 13f) is dissolved in 100 ml of distilled water, and the resulting solution is brought to a pH of 4.0 by mixing with 1 molar aqueous hydrochloric acid. At 80° C., it is now mixed in portions with 0.25 g (2.22 mmol) of manganese(II) carbonate. Then, the thus obtained reaction solution is refluxed for 5 hours. After cooling to room temperature, the pH of the aqueous product solution is set at 7.2 by mixing with 1N sodium hydroxide solution while being stirred vigorously and is desalinated via an AMICON(R) YM-3 ultrafiltration membrane (cut-off 3000 Da), and low-molecular components are removed. The retentate is then freeze-dried.

Yield: 1.80 g (92.0% of theory) of the title compound as a colorless lyophilizate.
H₂O content (Karl-Fischer): 7.28%
Elementary analysis (relative to anhydrous substance):

Cld:
C 38.07  H 3.25  F 18.28  Mn 6.22  N 6.34  Na 5.20  S 1.81
Fnd:
C 38.01  H 3.29  F 18.29  Mn 6.21  N 6.36  Na 5.28  S 1.78

EXAMPLE 14a
6-N-(Benzyloxycarbonyl)-2-N-[(N-pteroyl)-L-glutaminyl]-lysine-[1-(4-perfluorooctylsulfonyl)-piperazine]-amide 20 g (45.31 mmol) of folic acid is dissolved in 300 ml of dimethyl sulfoxide, and 9.49 g (46 mmol) of N,N-dicyclohexylcarbodiimide is added at 10° C. It is stirred overnight at room temperature. 29.1 g (35 mmol) of the title compound of Example 1c and 20 ml of pyridine are added to this mixture, and it is stirred for 3 hours at 50° C. It is cooled to room temperature, and a mixture of 1500 ml of diethyl ether/1500 ml of acetone is added. The deposited precipitate is filtered off and purified on (RP-18) (mobile solvent: gradient that consists of water/ethanol/tetrahydrofuran).

Yield: 21.59 g (38% of theory) of yellow solid.
Water content: 2.1%
Elementary analysis (relative to anhydrous substance):
Cld:  C 43.10  H 3.54  F 25.76  N 11.29  S 2.56
Fnd:  C 43.02  H 3.62  F 25.68  N 11.21  S 2.48

EXAMPLE 14b
2-N-[(N-pteroyl)-L-glutaminyl]-lysine-[1-(4-perfluorooctylsulfonyl)-piperazine]-amide 200 ml of hydrobromic acid in glacial acetic acid (48%) is added to 20 g (15.95 mmol) of the title compound of Example 14a, and it is stirred for 2 hours at 40° C. It is cooled to 0° C., 2000 ml of diethyl ether is added in drops, and the precipitated solid is filtered off. After drying in a vacuum (600° C.), 18.96 g (99% of theory) of a yellow-colored, crystalline solid is obtained.

Elementary analysis:
Cld:  C 37.01  H 3.27  Br 5.65  F 26.90  N 12.83  S 2.67
Fnd:  C 36.91  H 3.42  Br 6.31  F 29.75  N 12.72  S 2.56

EXAMPLE 14c
6-N-[1,4,7-tris(Carboxylatomethyl)-1,4,7,10-tetraazacyclododecane-10-(Pentanoyl-3-aza-4-oxo-5-methyl-5yl]-2-N-[(N-pteroyl)-L-glutaminyl]-lysine-[1-(4-perfluorooctylsulfonyl)-piperazine]-amide, Gd-complex 0.92 g (8 mmol) of N-hydroxysuccinimide, 0.68 g (16 mol) of lithium chloride and 5.04 g (8 mmol) of 1,4,7-tris(Carboxylatomethyl-10-(3-aza-4-oxo-5-methyl-5-yl)-1,4,7–10-tetraazacyclododecane, Gd-complex, are dissolved in 80 ml of dimethyl sulfoxide while being heated slightly. At 10° C., 2.06 g (10 mol) of N,N-dicyclohexylcarbodiimide is added, and it is then stirred for 3 hours at room temperature. 5 g (4.16 mmol) of the title compound of Example 14b and 10 ml of pyridine are added to this reaction solution, and it is stirred overnight at room temperature. The solution is poured into 1000 ml of acetone and stirred for 10 minutes. The precipitated solid is filtered off and then purified by chromatography (silica gel RP-18, mobile solvent: gradient that consists of water/ethanol/acetonitrile). It is dissolved in some water, the pH is set at 7.4 with sodium hydroxide solution and freeze-dried.

Yield: 3.87 g (53% of theory) of a yellow solid.
Water content: 5.8%
Elementary analysis (relative to anhydrous substance):
Cld:  C 38.36  H 3.74  F 18.42  Gd 8.97  N 12.78  Na 1.31  S 1.83
Fnd:  C 38.28  H 3.85  F 18.33  Gd 8.85  N 12.69  Na 1.42  S 1.75

EXAMPLE 15
a) 6-N-benzyloxycarbonyl-2-N-(3,6,9,12-tetraoxatridecanoyl)-lysine[1-(4-perfluorooctylsulfonyl)-piperazine]-amide A solution that consists of 16.85 g (70 mmol) of 3,6,9,12 tetraoxatridecanoic acid chloride in 50 ml of dichloromethane is added in drops at 0° C. to 50 g (60.20 mmol) of the title compound of Example 1c and 7.10 g (70 mmol) of triethylamine, dissolved in 350 ml of dichloromethane, and it is stirred for 3 hours at 0° C. 200 ml of 5% aqueous hydrochloric acid is added, and it is stirred for 5 minutes at room temperature. The organic phase is separated, dried on magnesium sulfate and evaporated to the dry state in a vacuum. The residue is chromatographed on silica gel (mobile solvent: dichloromethane/acetone=15:1).

Yield: 30.94 g (92% of theory) of a colorless, viscous oil.
Elementary analysis:
Cld:  C 40.63  H 4.19  F 31.21  N 5.41  S 3.10
Fnd:  C 40.75  H 4.08  F 31.29  N 5.58  S 3.25 b) 2-N-(3,6,9,12-tetraoxatridecanoyl)-lysine[1-(4-perfluorooctylsulfonyl)-piperazine]-amide 53.96 g (52.15 mmol) of the title compound of Example 15a is dissolved in 500 ml of ethanol, and 6 g of palladium catalyst (10% Pd/C) is added. It is hydrogenated at room temperature. Catalyst is filtered out, and the filtrate is evaporated to the dry state in a vacuum.

Yield: 43.0 g (quantitative) of a colorless solid.
Elementary analysis:
Cld:  C 36.01  H 4.14  F 35.86  N 6.22  S 3.56
Fnd:  C 27.60  H 5.13  F 39.09  N 6.68  S 3.81 c) 6-N-[1,4,7-tris(Carboxylatomethyl)-1,4,7,10-tetraazacyclododecane-10-(Pentanoyl-3-aza-4-oxo-5-methyl-5-yl)]-2-N-(3,6,9,12-tetraoxatridecanoyl)-lysine[1-(4-perfluorooctylsulfonyl)-piperazine]-amide, Gd complex 21.84 g (24.25 mmol) of the title compound of Example 15b, 2.79 g (24.25 mmol) of N-hydroxysuccinimide, 2.12 g (50 mmol) of lithium chloride and 15.27 g (24.25 mmol) of 1,4,7-tris(Carboxylatomethyl)-10-[(3-aza-4-oxo-5-methyl-5-yl)]-pentanoic acid]-1,4,7,10-tetraazacyclodecane, Gd complex, are dissolved in 200 ml of dimethyl sulfoxide while being heated slightly. At 10° C., 8.25 g (40 mmol) of N,N-dicyclohexyl-carbodiimide is added, and it then is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 28.21 g (81% of theory) of a colorless solid.
Water content: 11.0%
Elementary analysis
(relative to anhydrous substance):

| | | | | | | |
|---|---|---|---|---|---|---|
| Cld: | C 36.53 | H 4.33 | F 21.36 | N 8.34 | S 2.12 | Gd 10.40 |
| Fnd: | C 31.74 | H 4.98 | F 22.39 | N 8.69 | S 2.15 | Gd 10.87 |

EXAMPLE 16 a) 6-N-benzyloxycarbonyl-2-N-(Propyl-3-sulfonic Acid)-lysine[1-(4-perfluorooctyl-sulfonyl)-piperazine]-amide A solution that consists of 7.33 g (60 mol) of propane sultone in 50 ml of tetrahydrofuran is added in drops at 50° C. to 50 g (60.20 mmol) of the title compound of Example 1c and 7.10 g (70 mmol) of triethylamine, dissolved in 250 ml of dry tetrahydrofuran, and it is stirred for 3 hours at 60° C. 200 ml of 5% aqueous hydrochloric acid is added, and it is stirred for 5 minutes at room temperature. The organic phase is separated, dried on magnesium sulfate and evaporated to the dry state in a vacuum. The residue is chromatographed on silica gel (mobile solvent: dichloromethane/acetone=15:1).

Yield: 45.16 g (79% of theory) of a colorless, viscous oil.
Elementary analysis:

| | | | | | |
|---|---|---|---|---|---|
| Cld: | C 36.56 | H 3.49 | F 33.90 | N 5.88 | S 6.73 |
| Fnd: | C 36.72 | H 3.35 | F 33.79 | N 5.78 | S 6.75 | b) 2-N-(Propyl-3-sulfonic Acid)-lysine[1-(4-perfluorooctylsulfonyl)-piperazine]-amide 49.68 g (52.15 mmol) of the title compound of Example 16a is dissolved in 500 ml of ethanol, and 6 g of palladium catalyst (10% Pd/C) is added. It is hydrogenated at room temperature. Catalyst is filtered out, and the filtrate is evaporated to the dry state in a vacuum.

Yield: 42.69 g (quantitative) of a colorless solid.
Elementary analysis:

| | | | | | |
|---|---|---|---|---|---|
| Cld: | C 30.81 | H 3.32 | F 39.46 | N 6.84 | S 7.83 |
| Fnd: | C 30.64 | H 4.1 | F 39.29 | N 6.68 | S 7.89 | c) 6-N-[1,4,7-tris(Carboxylatomethyl)-1,4,7,10-tetraazacyclododecane-10-(Pentanoyl-3-aza-4-oxo-5-methyl-5-yl)]-2-N-(Propyl-3-sulfonic Acid)-lysine[1-(4-perfluorooctylsulfonyl)-piperazine]-amide, Gd complex 19.85 g (24.25 mmol) of the title compound of Example 16b, 2.79 g (24.25 mmol) of N-hydroxysuccinimide, 2.12 g (50 mmol) of lithium chloride and 15.27 g (24.25 mmol) of 1,4,7-tris(Carboxylatomethyl)-10-[(3-aza-4-oxo-5-methyl-5-yl)]-pentanoic acid]-1,4,7,10-tetraazacyclodecane, Gd complex, are dissolved in 200 ml of dimethyl sulfoxide while being heated slightly. At 10° C., 8.25 g (40 mmol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 28.13 g (81% of theory) of a colorless solid.
Water content: 11.0%
Elementary analysis
(relative to anhydrous substance):

| | | | | | | |
|---|---|---|---|---|---|---|
| Cld: | C 33.27 | H 3.70 | F 22.36 | N 8.73 | S 4.44 | Gd 10.89 |
| Fnd: | C 32.41 | H 3.88 | F 22.49 | N 8.69 | S 4.35 | Gd 10.97 |

EXAMPLE 17 a) 6-N-benzyloxycarbonyl-2-N,N-bis(Propyl-3-sulfonic Acid)-lysine[1-(4-perfluorooctylsulfonyl)-piperazine]-amide A solution that consists of 14.65 g (120 mmol) of 1,3-propane sultone in 100 ml of tetrahydrofuran is added in drops at 50° C. to 50 g (60.20 mmol) of the title compound of Example 1c and 12.14 g (120 mmol) of triethylamine, dissolved in 250 ml of dry tetrahydrofuran, and it is stirred for 3 hours at 60° C. 400 ml of 5% aqueous hydrochloric acid is added, it is stirred for 5 minutes at room temperature, mixed with sodium chloride, the organic phase is separated, dried on magnesium sulfate, and it is evaporated to the dry state in a vacuum. The residue is chromatographed on silica gel (mobile solvent: dichloromethane/acetone=15:1).

Yield: 52.24 g (81% of theory) of a colorless, viscous oil.
Elementary analysis:

| | | | | | |
|---|---|---|---|---|---|
| Cld: | C 35.76 | H 3.66 | F 30.05 | N 5.21 | S 8.95 |
| Fnd: | C 35.75 | H 3.55 | F 30.19 | N 5.08 | S 9.04 | b) 2-N,N Bis(Propyl-3-sulfonic Acid)-lysine[1-(4-perfluorooctylsulfonyl)-piperazine]-amide 53.74 g (52.15 mmol) of the title compound of Example 17a is dissolved in 500 ml of ethanol, and 6 g of palladium catalyst (10% Pd/C) is added. It is hydrogenated at room temperature. Catalyst is filtered out, and the filtrate is evaporated to the dry state in a vacuum.

Yield: 49.06 g (quantitative) of a colorless solid.
Elementary analysis:

| | | | | | |
|---|---|---|---|---|---|
| Cld: | C 30.64 | H 3.54 | F 34.33 | N 5.96 | S 10.23 |
| Fnd: | C 30.69 | H 3.71 | F 34.19 | N 6.08 | S 10.38 | c) 6-N-[1,4,7-tris(Carboxylatomethyl)-1,4,7,10-tetraazacyclododecane-10-(Pentanoyl-3-aza-4-oxo-5-methyl-5-yl)]-2-N,N bis(Propyl-3-sulfonic Acid)-lysine[1-(4-perfluorooctylsulfonyl)-piperazine]-amide, Gd complex, Disodium Salt 38.76 g (24.25 mmol) of the title compound of Example 17b, 2.79 g (24.25 mmol) of N-hydroxysuccinimide, 2.12 g (50 mmol) of lithium chloride and 15.27 g (24.25 mmol) of 1,4,7-tris(Carboxylatomethyl)-10-[(3-aza-4-oxo-5-methyl-5-yl)]-pentanoic acid]-1,4,7,10-tetraazacyclodecane, Gd complex, are dissolved in 200 ml of dimethyl sulfoxide while being heated slightly. At 10° C., 8.25 g (40 mmol) of N,N-dicyclohexylcarbodiimide is added, and it then is stirred overnight at room temperature. The solution is poured into 3000 ml of acetone, and it is stirred for 10 minutes. The precipitated solid is filtered off, and then purified by chromatography (silica gel RP-18, mobile solvent: gradient that consists of water/ethanol/acetonitrile).

| Yield: | 31.63 g (81% of theory) of a colorless solid. | | | | | |
|---|---|---|---|---|---|---|
| Water content: | 11.0% | | | | | |
| Elementary analysis (relative to anhydrous substance): | | | | | | |
| Cld: | | | | | | |
| C 32.07 | H 3.57 | F 20.06 | N 7.83 | S 5.97 | Gd 9.76 | Na 2.86 |
| Fnd: | | | | | | |
| C 31.94 | H 3.48 | F 20.19 | N 7.69 | S 5.85 | Gd 9.87 | Na 2.99 |

EXAMPLE 18 a) N-trifluoroacetyl-L-glutamic Acid-5-benzyl Ester 100 g (421.5 mmol) of L-glutamic Acid-5-benzyl ester is dissolved in a mixture that consists of 1000 ml of trifluoroacetic acid ethyl ester/500 ml of ethanol, and it is stirred for 24 hours at room temperature. It is evaporated to the dry state, and the residue is crystallized from diisopropyl ether.

| Yield: 140.47 g (96% of theory) of a colorless, crystalline powder. | | | | |
|---|---|---|---|---|
| Elementary analysis: | | | | |
| Cld: | C 50.46 | H 4.23 | F 17.10 | N 4.20 |
| Fnd: | C 51.35 | H 4.18 | F 17.03 | N 4.28 | b) 2-N-trifluoroacetyl-L-glutamic Acid-5-benzyl Ester-N-bis(2-hydroxyethyl)-amide 8.25 g (40 mmol) of N,N-dicyclohexylcarbodiimide is added at 0° C. to a solution that consists of 24.9 g (24.08 mmol) of the title compound of Example 18a, 2.53 g (24.08 mmol) of diethanolamine and 2.77 g (24.08 mmol) of N-hydroxysuccinimide, dissolved in 150 ml of dimethylformamide. It is stirred for 3 hours at 0° C., then overnight at room temperature. Precipitated urea is filtered out, the filtrate is evaporated to the dry state in a vacuum and chromatographed on silica gel (mobile solvent= dichloromethane/ethanol=20:1).

| Yield: | 9.11 g (90% of theory) of a viscous oil. | | | |
|---|---|---|---|---|
| Elementary analysis: | | | | |
| Cld: | C 51.43 | H 5.51 | F 13.56 | N 6.66 |
| Fnd: | C 51.22 | H 5.41 | F 13.40 | N 6.75 | c) N-trifluoroacetyl-L-glutamic Acid-N Bis(2-hydroxyethyl)-monoamide 21.92 g (52.15 mmol) of the title compound of Example 18b is dissolved in 500 ml of ethanol, and 3 g of palladium catalyst (10% Pd/C) is added. It is hydrogenated at room temperature. Catalyst is filtered out, and the filtrate is evaporated to the dry state in a vacuum.

| Yield: | 43.0 g (quantitative) of a colorless solid. | | | |
|---|---|---|---|---|
| Elementary analysis: | | | | |
| Cld: | C 40.01 | H 5.19 | F 17.26 | N 8.48 |
| Fnd: | C 39.84 | H 5.13 | F 17.09 | N 8.68 | d) Trifluoroacetyl-L-glutamic Acid-N-bis(2-hydroxyethyl)-amide-5-[1-(4-perfluorooctylsulfonyl)-piperazine-amide 16.42 g (66.4 mmol) of EEDQ (2-ethoxy-1,2-dihydroquinoline-1-carboxylic acid ethyl ester) is added at 0° C. to 10.96 g (33.2 mmol) of the title compound of Example 18a and 18.87 g (33.2 mmol) of 1-perfluorooctylsulfonyl-piperazine (produced according to DE 19603033) in 80 ml of tetrahydrofuran, and it is stirred overnight at room temperature. It is evaporated to the dry state in a vacuum and chromatographed on silica gel (mobile solvent: dichloromethane/methanol=20:1).

| Yield: | 30.93 g (93% of theory) of a colorless solid. | | | | |
|---|---|---|---|---|---|
| Elementary analysis: | | | | | |
| Cld: | C 39.61 | H 2.89 | F 35.66 | N 6.19 | S 3.54 |
| Fnd: | C 39.68 | H 2.74 | F 35.81 | N 6.13 | S 3.40 | e) L-Glutamic Acid-N-bis(2-hydroxyethyl)-amide-5-[1-(4-perfluorooctylsulfonyl)-piperazine]-amide Ammonia gas is introduced at 0° C. for one hour into a solution that consists of 30.24 g (30.22 mmol) of the title compound of Example 18b in 200 ml of ethanol. It then is stirred for 4 hours at 0° C. It is evaporated to the dry state, and the residue is absorptively precipitated from water. The solid is filtered off, and it is dried in a vacuum (50° C.)

| Yield: | 26.55 g (97% of theory) of an amorphous solid. | | | | |
|---|---|---|---|---|---|
| Elementary analysis: | | | | | |
| Cld: | C 41.12 | H 2.89 | F 35.66 | N 6.19 | S 3.54 |
| Fnd: | C 41.15 | H 2.83 | F 35.78 | N 6.28 | S 3.71 | f) N-[1,4,7-tris(Carboxylatomethyl)-1,4,7,10-tetraazacyclododecane-10-(Pentanoyl-3-aza-4-oxo-5-methyl-5-yl)]-L-glutamic Acid-N-bis (2-hydroxyethyl)-amide-5-[1-(4-perfluorooctylsulfonyl)-piperazine]-amide, Gd Complex 211.96 g (24.25 mmol) of the title compound of Example 18e, 2.79 g (24.25 mmol) of N-hydroxysuccinimide, 2.12 g (50 mmol) of lithium chloride and 15.27 g (24.25 mmol) of 1,4,7-tris (Carboxylatomethyl)-10-[(3-aza-4-oxo-5-methyl-5-yl)]-pentanoic acid]-1,4,7,10-tetraazacyclododecane, Gd complex, are dissolved in 200 ml of dimethyl sulfoxide while being heated slightly. At 10° C., 8.25 g (40 mmol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile)

Yield: 27.43 g (81% of theory) of a colorless solid.
Water content: 11.0%
Elementary analysis
(relative to anhydrous substance):

| Cld: | C 34.41 | H 3.83 | F 23.13 | N 9.03 | S 2.30 | Gd 11.26 |
|---|---|---|---|---|---|---|
| Fnd: | C 34.34 | H 3.98 | F 23.29 | N 9.19 | S 2.15 | Gd 11.07 |

EXAMPLE 19 a) N-trifluoroacetyl-L-glutamic Acid-5-benzylester-N-dimethyl-bis(1,1-dihydroxymethyl)-amide 8.25 g (40 mmol) of N,N-dicyclohexylcarbodiimide is added at 0° C. to a solution that consists of 8.03 g (24.08 mmol) of the title compound of Example 18a, 3.98 g (24.08 mmol) of dimethyl-bis(1,1-dihydroxymethyl)-amine and 2.77 g (24.08 mmol) of N-hydroxysuccinimide, dissolved in 150 ml of dimethylformamide. It is stirred for 3 hours at 0° C., then overnight at room temperature. Precipitated urea is filtered out, the filtrate is evaporated to the dry state in a vacuum and chromatographed on silica gel (mobile solvent: dichloromethane/ethanol=20:1).

Yield: 110.53 g (91% of theory) of a viscous oil.
Elementary analysis:

| Cld: | C 50.00 | H 5.66 | F 11.86 | N 7.18 |
|---|---|---|---|---|
| Fnd: | C 50.17 | H 5.82 | F 11.80 | N 7.15 | b) N-trifluoroacetyl-L-glutamic Acid-5-benzyl ester-[1-(4-perfluorooctylsulfonyl)-piperazine]-amide 25.05 g (52.15 mmol) of the title compound of Example 19a is dissolved in 500 ml of ethanol, and 6 g of palladium catalyst (10w Pd/C) is added. It is hydrogenated at room temperature. Catalyst is filtered out, and the filtrate is evaporated to the dry state in a vacuum.

Yield: 20.36 g (quantitative) of a colorless solid.
Elementary analysis:

| Cld: | C 40.00 | H 5.42 | F 14.60 | N 7.18 |
|---|---|---|---|---|
| Fnd: | C 40.10 | H 5.53 | F 14.69 | N 7.28 | c) N-trifluoroacetyl-L-glutamic Acid-N-dimethyl-bis(1,1-dihydroxymethyl)-amide-5-[1-(4-perfluorooctyl-sulfonyl) Piperazine]-amide 16.42 g (66.4 mmol) of EEDQ (2-ethoxy-1,3-dihydroquinoline-1-carboxylic acid ethyl ester) is added to 12.96 g (33.2 mmol) of the title compound of Example 19b and 18.87 g (33.2 mmol) of 1-perfluorooctylsulfonyl-piperazine (produced according to DE 19603033) in 800 ml of tetrahydrofuran, and it is stirred overnight at room temperature. It is evaporated to the dry state in a vacuum and chromatographed on silica gel (mobile solvent: dichloromethane/methanol=20:1).

Yield: 28.42 g (91% of theory) of a colorless solid.
Elementary analysis:

| Cld: | C 31.93 | H 3.00 | F 40.40 | N 5.96 | S 3.41 |
|---|---|---|---|---|---|
| Fnd: | C 32.08 | H 2.94 | F 40.57 | N 5.88 | S 3.31 | d) L-Glutamic Acid-N-[dimethyl-bis(1,1,-dihydroxymethyl)]-amide-5-[(1-4-perfluorooctylsulfonyl)-piperazine]-amide Ammonia gas is introduced at 0° C. for one hour into a solution that consists of 28.41 g (30.2 mmol) of the title compound of Example 19c in 200 ml of ethanol. It then is stirred for 4 hours at 0° C. It is evaporated to the dry state, and the residue is absorptively precipitated from water. The solid is filtered off and dried in a vacuum (50° C.)

Yield: 24.74 g (97% of theory) of an amorphous solid.
Elementary analysis:

| Cld: | C 32.71 | H 3.46 | F 38.24 | N 6.63 | S 3.80 |
|---|---|---|---|---|---|
| Fnd: | C 32.75 | H 3.33 | F 38.38 | N 6.68 | S 3.81 | e) 2-N-[1,4,7-tris(Carboxylatomethyl)-1,4,7,10-tetraazacyclododecane-10-(Pentanoyl-3-aza-4-oxo-5-methyl-5-yl)]-L-glutamic Acid-N-[dimethyl-bis(1,1-dihydroxymethyl)-amide]-5-[1-(4-perfluorooctylsulfonyl)-piperazine]-amide, Gd Complex 20.48 g (24.25 mmol) of the title compound of Example 19d, 2.79 g (24.25 mmol) of N-hydroxysuccinimide, 2.12 g (50 mmol) of lithium chloride and 15.27 g (24.25 mmol) of 1,4,7-tris(Carboxylatomethyl)-10-[(3-aza-4-oxo-5-methyl-5-yl)]-pentanoic acid]-1,4,7,10-tetraazacyclododecane, Gd complex, are dissolved in 200 ml of dimethyl sulfoxide while being heated slightly. At 10° C., 8.25 g (40 mmol) of N,N-dicyclohexyl-carbodiimide is added, and it then is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 29.05 g (83% of theory) of a colorless solid.
Water content: 11.0%
Elementary analysis
(relative to anhydrous substance):

| Cld: | C 34.12 | H 3.91 | F 22.38 | N 8.73 | S 2.22 | Gd 10.90 |
|---|---|---|---|---|---|---|
| Fnd: | C 34.24 | H 3.98 | F 22.39 | N 8.69 | S 2.15 | Gd 10.87 |

EXAMPLE 20 a) N-trifluoromethylacetyl-L-glutamic Acid-5-benzylester-[1-(4-perfluorooctylsulfonyl)-piperazine]-amide 16.42 g (66.4 mmol) of EEDQ (2-ethoxy-1,2-dihydroquinoline-1-carboxylic acid ethyl ester) is added at 0° C. to 11.06 g (33.2 mmol) of the title compound of Example 18a and 18.87 g (33.2 mmol) of 1-perfluorooctylsulfonyl-piperazine (produced according to DE 19603033) in 80 ml of tetrahydrofuran, and it is stirred overnight at room temperature. It is evaporated to the dry state in a vacuum and chromatographed on silica gel (mobile solvent: dichloromethane/methanol=20:1).

| Yield: | 27.28 g (93% of theory) of a colorless solid. | | | | |
|---|---|---|---|---|---|
| Elementary analysis: | | | | | |
| Cld: | C 35.35 | H 2.40 | F 43.01 | N 4.76 | S 3.63 |
| Fnd: | C 35.48 | H 2.51 | F 42.87 | N 4.73 | S 3.50 | b) N-trifluoroacetyl-L-glutamic Acid-5-[1-[4-perfluorooctylsulfonyl)-piperazine]-amide 21.92 g (52.15 mmol) of the title compound of Example 18a is dissolved in 500 ml of ethanol, and 3 g of palladium catalyst (10% Pd/C) is added. It is hydrogenated at room temperature. Catalyst is filtered out, and the filtrate is evaporated to the dry state in a vacuum.

| Yield: | 41.37 g (quantitative) of a colorless solid. | | | | |
|---|---|---|---|---|---|
| Elementary analysis: | | | | | |
| Cld: | C 28.76 | H 1.91 | F 47.89 | N 5.30 | S 4.04 |
| Fnd: | C 28.84 | H 2.03 | F 47.79 | N 5.28 | S 4.19 | c) N-trifluoroacetyl-L-glutamic Acid-N-bis(2-hydroxyethyl)-amide-5-[1-(4-perfluorooctyl-sulfonyl)-piperazine]-amide 8.25 g (40 mmol) of N,N-dicyclohexylcarbodiimide is added at 0° C. to a solution that consists of 24.9 g (24.08 mmol) of the title compound of Example 18a, 2.53 g (24.08 mmol) of diethanolamine and 2.77 g (24.08 mmol) of N-hydroxysuccinimide, dissolved in 150 ml of dimethylformamide. It is stirred for 3 hours at 0° C., then overnight at room temperature. Precipitated urea is filtered out, the filtrate is evaporated to the dry state in a vacuum and chromatographed on silica gel (mobile solvent=dichloromethane/ethanol 20:1).

| Yield: | 9.11 g (90% of theory) of a viscous oil. | | | | |
|---|---|---|---|---|---|
| Elementary analysis: | | | | | |
| Cld: | C 31.37 | H 2.75 | F 43.15 | N 6.36 | S 3.64 |
| Fnd: | C 31.22 | H 2.61 | F 43.30 | N 6.25 | S 3.81 | d) L-glutamic Acid-N-bis(2-hydroxyethyl)-amide-5-[1-(4-perfluorooctylsulfonyl)-piperazine]-amide Ammonia gas is introduced at 0° C. for one hour into a solution that consists of 26.61 g (30.22 mmol) of the title compound of Example 18c in 200 ml of ethanol. It then is stirred for 4 hours at 0° C. It is evaporated to the dry state, and the residue is absorptively precipitated from water. The solid is filtered off and dried in a vacuum (50° C.).

| Yield: | 23.93 g (97% of theory) of an amorphous solid. | | | | |
|---|---|---|---|---|---|
| Elementary analysis: | | | | | |
| Cld: | C 30.89 | H 3.09 | F 39.56 | N 6.86 | S 3.93 |
| Fnd: | C 30.75 | H 3.13 | F 39.78 | N 6.75 | S 3.81 | e) N-[1,4,7-tris(Carboxylatomethyl)-1,4,7,10-tetraazacyclododecane-10-(Pentanoyl-3-aza-4-oxo-5-methyl-5-yl)]-L-glutamic Acid-N-bis(2-hydroxyethyl)-amide-5-[1-(4-perfluorooctylsulfonyl)-piperazine]-amide, Gd Complex 16.43 g (24.25 mmol) of the title compound of Example 20d, 2.79 g (24.25 mmol) of N-hydroxysuccinimide, 2.12 g (50 mmol) of lithium chloride and 15.27 g (24.25 mmol) of 1,4,7-tris(Carboxylatomethyl)-10-[(3-aza-4-oxo-5-methyl-5-yl)]-pentanoic acid]-1,4,7,10-tetraazacyclododecane, Gd complex, are dissolved in 200 ml of dimethyl sulfoxide while being heated slightly. At 10° C., 8.25 g (40 mmol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

| Yield: | 28.10 g (83% of theory) of a colorless solid. | | | | | |
|---|---|---|---|---|---|---|
| Water content: | 11.0% | | | | | |
| Elementary analysis | | | | | | |
| (relative to anhydrous substance): | | | | | | |
| Cld: | C 34.41 | H 3.83 | F 23.13 | N 9.03 | S 2.30 | Gd 11.26 |
| Fnd: | C 34.44 | H 4.98 | F 23.19 | N 8.89 | S 2.15 | Gd 11.17 |

EXAMPLE 21 a) N-trifluoroacetyl-glutamic Acid-5-benzylester-[1-(4-perfluorooctylsulfonyl)-piperazine]-amide 16.42 g (66.4 mmol) of EEDQ (2-ethoxy-1,2-dihydroquinoline-1-carboxylic acid ethyl ester) is added at 0° C. to 11.06 g (33.2 mmol) of the title compound of Example 18a and 18.87 g (33.2 mmol) of 1-perfluorooctylsulfonyl-piperazine (produced according to DE 19603033) in 80 ml of tetrahydrofuran, and it is stirred overnight at room temperature. It is evaporated to the dry state in a vacuum and chromatographed on silica gel (mobile solvent: dichloromethane/methanol=20:1).

| Yield: | 27.28 g (93% of theory) of a colorless solid. | | | | |
|---|---|---|---|---|---|
| Elementary analysis: | | | | | |
| Cld: | C 35.35 | H 2.40 | F 43.01 | N 4.76 | S 3.63 |
| Fnd: | C 35.48 | H 2.54 | F 42.87 | N 4.73 | S 3.40 | b) N-trifluoroacetyl-L-glutamic Acid-5-[1-[4-perfluorooctylsulfonyl)-piperazine]-amide 21.92 g (52.15 mmol) of the title compound of Example 21a is dissolved in 500 ml of ethanol, and 3 g of palladium catalyst (10% Pd/C) is added. It is hydrogenated at room temperature. Catalyst is filtered out, and the filtrate is evaporated to the dry state in a vacuum.

| Yield: | 41.37 g (quantitative) of a colorless solid. | | | | |
|---|---|---|---|---|---|
| Elementary analysis: | | | | | |
| Cld: | C 28.76 | H 1.91 | F 47.89 | N 5.30 | S 4.04 |
| Fnd: | C 28.84 | H 1.81 | F 47.79 | N 5.28 | S 4.16 |

EXAMPLE 22

Organ Distribution (Including Tumor and Lymph Node Concentration) After Intravenous Administration of the Contrast Medium According to the Invention From Example 3 in Prostate-cancer-Carrying Rats.

After intravenous administration of 100 μmol of total gadolinium/kg of body weight of the title compound of Example 3 in rats (Cop-inbreeding Dunning R3327 MAT-Lu prostate cancer i.m.-implanted 12 days earlier), the metal content in various organs, in tumors and in lymph nodes (pooled as mesenteral and peripheral lymph nodes) was determined 10 minutes, 1 and 24 hours after administration (MW=SD, n=3).

| | Gd-Konzentration [μmol/l] | | | % Dosis pro Gesamtgewebe | | |
|---|---|---|---|---|---|---|
| | 10 min p.i. | 1 h p.i. | 24 h p.i. | 10 min p.i. | 1 h p.i. | 24 h p.i. |
| Leber | 137 ± 39 | 136 ± 1 | 172 ± 6 | 3,79 ± 1,12 | 3,93 ± 0,20 | 5,37 ± 0,63 |
| Milz | 184 ± 58 | 161 ± 3 | 161 ± 19 | 0,25 ± 0,07 | 0,23 ± 0,01 | 0,25 ± 0,01 |
| Pankreas | 99 ± 26 | 95 ± 15 | 55 ± 7 | 0,25 ± 0,08 | 0,23 ± 0,07 | 0,18 ± 0,01 |
| Niere | 359 ± 88 | 394 ± 41 | 292 ± 18 | 1,70 ± 0,39 | 2,00 ± 0,21 | 1,38 ± 0,07 |
| Lunge | 344 ± 95 | 321 ± 16 | 146 ± 19 | 1,30 ± 0,33 | 1,27 ± 0,05 | 0,56 ± 0,03 |
| Herz | 177 ± 46 | 151 ± 7 | 65 ± 12 | 0,40 ± 0,11 | 0,33 ± 0,01 | 0,15 ± 0,03 |
| Gehirn | 16 ± 5 | 16 ± 3 | 5 ± 0 | 0,09 ± 0,02 | 0,10 ± 0,02 | 0,03 ± 0,00 |
| Muskel** | 41 ± 12 | 40 ± 4 | 13 ± 2 | 0,12 ± 0,04 | 0,08 ± 0,01 | 0,03 ± 0,01 |
| Tumor | 82 ± 32 | 126 ± 10 | 100 ± 6 | 0,20 ± 0,07 | 0,40 ± 0,12 | 0,46 ± 0,42 |
| Femur | 61 ± 10 | 64 ± 5 | 33 ± 1 | 0,50 ± 0,06 | 0,50 ± 0,02 | 0,26 ± 0,01 |
| mes. LK | 155 ± 40 | 160 ± 5 | 127 ± 7 | 0,11 ± 0,04 | 1,10 ± 0,01 | 0,09 ± 0,01 |
| periph. LK | 115 ± 27 | 186 ± 6 | 108 ± 6 | 0,13 ± 0,03 | 0,19 ± 0,03 | 0,11 ± 0,02 |
| Magen (entleert) | 90 ± 26 | 93 ± 3 | 48 ± 8 | 0,47 ± 0,16 | 0,50 ± 0,06 | 0,27 ± 0,03 |
| Darm (entleert) | 146 ± 37 | 130 ± 7 | 101 ± 12 | 2,48 ± 0,56 | 1,85 ± 0,27 | 1,63 ± 0,15 |
| Blut* | 621 ± 137 | 534 ± 12 | 169 ± 16 | 35,18 ± 7,43 | 30,63 ± 1,05 | 9,58 ± 1,02 |
| Restkörper | — ± — | — ± — | 103 ± 7 | — ± — | — ± — | 31,05 ± 4,60 |
| Harn 0–24 h | — - | — - | 60 ± 19 | — - | — - | 36,38 ± 2,36 |
| Faeces 0–24 h | — - | — - | 561 ± 28 | — - | — - | 8,91 ± 2,29 |
| Summe der Organe*** | | | | 46,35 ± 9,98 | 41,79 ± 1,76 | 50,95 ± 4,52 |
| Bilanz | — | — | — | ± | ± | 96,24 ± 3,47 |

*58 ml Blut/kg KGW
**nur Gewebealiquot v. rechten Unterschenkelmuskel
***Summe Organe 10 und 60 min p.i. ohne Restkörper

[Key to Table:]
Gd-Konzentration [μmol/l] = Gd-concentration [μmol/l]
% Dosis pro Gesamtgewebe = % dose per total tissue
Leber = liver
Milz = spleen
Pankreas = pancreas
Niere = kidney
Lunge = lung
Herz = heart
Gehirn = brain
Muskel = muscle
Tumor = tumor
Femur = femur
mes. LK = mes. LK
Periph. LK = periph. LK
Magen (entleert) = Stomach (emptied)
Darm (entleert) = intestine (emptied)
Blut* = blood*
Restkörper = remainder of the body
Harn 0–24 h = Urine 0–24 hours
Faeces 0–24 h = Feces 0–24 hours
Summe der Organe = The sum total of all of the organs
Bilanz = balance
*58 ml Blut/kg KGW = 58 ml of blood/kg of body weight
**nur Gewebealiquot v. rechten unterschenkelmuskel = only tissue sample from right lower leg muscle
***Summe Organe 10 und 60 min p.i. ohne Restkörper = the sum total of all of the organs at 10 and 60 min. p.i., less the remainder of the body In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. 100 40 858.3, filed Aug. 11, 2000 is hereby incorporated by reference.

What is claimed is:

1. Perfluoroalkyl-containing complexes with polar radicals of formula I

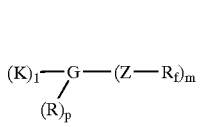

in which $R_f$ is a perfluorinated, straight-chain or branched carbon chain with the formula —$C_nF_{2n}E$, in which E is a terminal fluorine, chlorine, bromine, iodine or hydrogen atom, and n is a number from 4–30, K is a metal complex of formula II

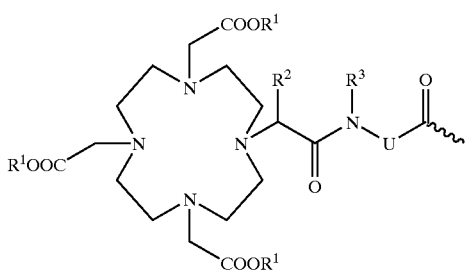

(II)

in which

R$^1$ is a hydrogen atom or a metal ion equivalent of atomic numbers 21–29, 31–33, 37–39, 42–44, 49 or 57–83, provided that at least two are R$^1$ are metal ion equivalents, R$^2$ and R$^3$, independently of one another, are hydrogen, C$_1$–C$_7$ alkyl, benzyl, phenyl, —CH$_2$OH or —CH$_2$OCH$_3$, and U is —C$_6$H$_4$—O—CH$_2$-ω-, —(CH$_2$)$_{1-5}$-ω, a phenylene group, —CH$_2$—NHCO—CH—CH(CH$_2$COOH)—C$_6$H$_4$-ω-, —C$_6$H$_4$—(OCH$_2$COOH)—CH$_2$-ω or a C$_1$–C$_{12}$ alkylene group or C$_7$–C$_{12}$—C$_6$H$_4$—O group that is optionally interrupted by one or more oxygen atoms, 1 to 3—NHCO groups or 1- to 3—CONH groups and/or is substituted with 1 to 3—(CH$_2$)$_{0.5}$COOH groups, whereby ω stands for the binding site to —CO—, or of fomuila III

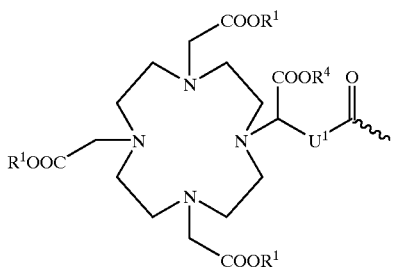

(III)

in which R$^1$ has the above-mentioned meaning, R$^4$ is hydrogen or a metal ion equivalent that is mentioned under R$^1$, and U$^1$ represents —C$_6$H$_4$—O—CH$_2$-ω-, whereby ω means the binding site to —CO—, or of formula IV

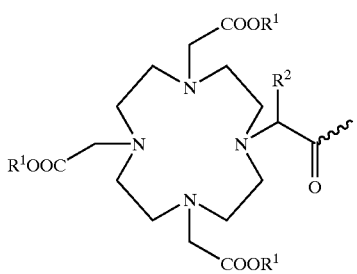

(IV)

in which R$^1$ and R$^2$ have the above-mentioned meaning or of formula V A of V B

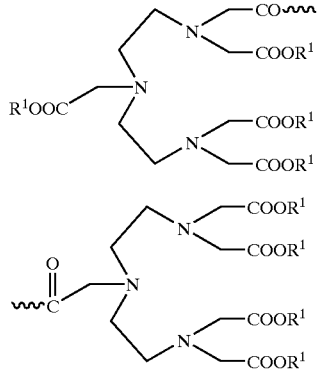

(V A)

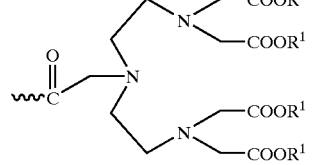

(V B)

in which R$^1$ has the above-mentioned meaning, or of formula VI

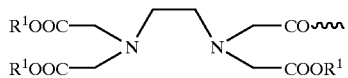

(VI)

in which R$^1$ has the above-mentioned meaning, or of formula VII

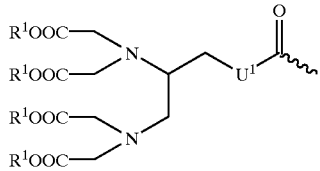

(VII)

in which R$^1$ has the above-mentioned meaning, and

U$^1$ is —C$_6$H$_4$—O—CH$_2$-ω-, whereby ω means the binding site to —CO—, and in radical K, optionally present free acid groups optionally can be present as salts of organic and/or inorganic bases or amino acids or amino acid amides, G is a radical that is functionalized in at least three places and that is selected from radicals a) to i) below:

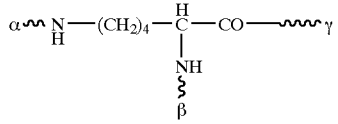

(a)

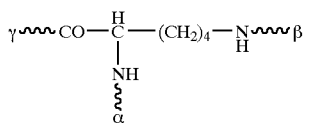

(b)

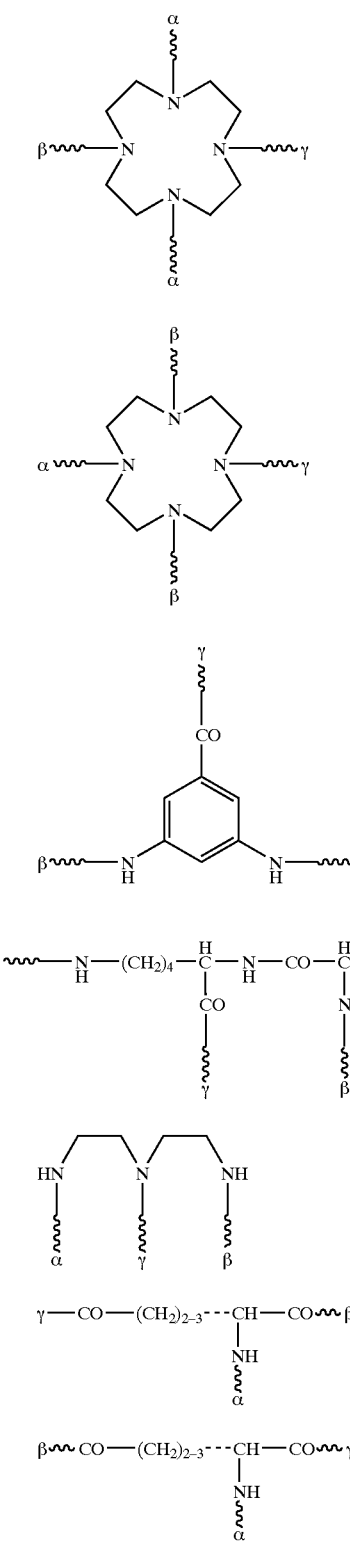

whereby α is the binding site of G to complex K, β is the binding site of G to radical R and γ represents the binding site of G to radical Z, Z is

γ—N⟨⟩N—SO$_2$—ε

γ-C(O)CH$_2$O(CH$_2$)$_2$-ξ, whereby γ is the binding site of Z to radical G, and ξ is the binding site of Z to perfluorinated radical R$_f$, R is:
  a polar radical selected from complexes K of formula II as to VII, whereby R$^1$ here is a hydrogen atom or a metal ion equivalent of atomic numbers 20–29, 31–33, 37–39, 42–44, 49 or 57–83, and radicals R$^2$, R$^3$, R$^4$, U and U$^1$ have the above-indicated meaning, with the proviso that, when G is the residue (c) or (d) and R is selected from formula II or V, R shall not be identical with K of formula I if Z stands for γ-C(O)CH$_2$O(CH$_2$)-ε, or
  a folic acid radical, or a carbon chain with 2–30 C-atoms that is bonded via —CO—, —SO$_2$— or a direct bond to radical G, in a straight line or branched, saturated or unsaturated, optionally interrupted by 1–10 oxygen atoms, 1–5 —NHCO groups, 1–5 —CONH groups, 1–2 sulfur atoms, 1–5 —NH groups or 1–2 phenylene groups, which phenylene groups optionally can be substituted with 1–2 OH groups, 1–2 NH$_2$ groups, 1–2 —COOH groups, or 1–2 —SO$_3$H groups, the carbon chain also optionally substituted with 1–8 OH groups, 1–5 —COOH groups, 1–2 SO$_3$H groups, 1–5 NH$_2$ groups, 1–5 C$_1$–C$_4$ alkoxy groups, and l, m, and p, independently of one another, mean the whole numbers 1 or 2.

2. Metal complexes according to claim 1, wherein metal ion equivalent R$^1$ in radical K is an element of atomic numbers 21–29, 39, 42, 44 or 57–83.

3. Metal complexes according to claim 1, wherein metal ion equivalent R$^1$ in radical K is an element of atomic numbers 27, 29, 31–33, 37–39, 43, 49, 62, 64, 70, 75 and 773.

4. Metal complexes according to claim 1, wherein K is a metal complex of formula II, III, VB or VII.

5. Metal complexes according to claim 1, wherein polar radical R has the meaning of complex K.

6. Metal complexes according to claim 5, wherein polar radical R is one of complexes K of formulas II, III, VA or VII.

7. Metal complexes according to claim 5, wherein R$^1$ is a metal ion equivalent of atomic numbers 20, 25 or 64.

8. Metal complexes according to claim 1, wherein polar radical R has one of the following meanings:
  —C(O)CH$_2$CH$_2$SO$_3$H
  —C(O)CH$_2$OCH$_2$CH$_2$OCH$_2$CH$_2$OH
  —C(O)CH$_2$OCH$_2$CH$_2$OH
  —C(O)CH$_2$OCH$_2$CH(OH)CH$_2$OH
  —C(O)CH$_2$NH—C(O)CH$_2$COOH
  —C(O)CH$_2$CH(OH)CH$_2$OH
  —C(O)CH$_2$OCH$_2$COOH
  —SO$_2$CH$_2$CH$_2$COOH
  —C(O)—C$_6$H$_3$—(m—COOH)$_2$
  —C(O)CH$_2$O—C$_6$H$_4$—m—SO$_3$H
  —C(O)CH$_2$NHC(O)CH$_2$NHC(O)CH$_2$OCH$_2$COOH
  —C(O)CH$_2$OCH$_2$CH$_2$OCH$_2$COOH —C(O)CH$_2$OCH$_2$CH(OH)CH$_2$O—CH$_2$CH$_2$OH
—C(O)CH$_2$OCH$_2$CH(OH)CH$_2$OCH$_2$—CH(OH)—CH$_2$OH
—C(O)CH$_2$SO$_3$H
—C(O)CH$_2$CH$_2$COOH
—C(O)CH(OH)CH(OH)CH$_2$OH
—C(O)CH$_2$O[(CH$_2$)$_2$O]$_{1-9}$—CH$_3$
—C(O)CH$_2$O[(CH$_2$)$_2$O]$_{1-9}$—H
—C(O)CH$_2$OCH(CH$_1$OH)$_2$
—C(O)CH$_2$OCH(CH$_2$OCH$_2$COOH)$_2$
—C(O)—C$_6$H$_3$—(m—OCH$_2$COOH)$_2$
—CO—CH$_2$O—(CH$_2$)$_2$O(CH$_2$)$_2$O—(CH$_2$)$_2$O(CH$_2$)OCH$_3$.

9. Metal complexes according to claim 1, wherein polar radical R is the folic acid radical.

10. Metal complexes according to claim 1, wherein G in formula I is a lysine radical (a) or (b).

11. Metal complexes according to claim 1, wherein U in metal complex K represents the group —CH$_2$— or —C$_6$H$_4$—O—CH$_2$-ω, whereby ω stands for the binding site to —CO—.

12. A method for the production of contrast media for use in NMR diagnosis or x-ray diagnosis, which comprises formulating a metal complex of claim 2 into a form suitable for NMR diagnosis or x-ray diagnosis.

13. A method for the production of contrast media for infarction or necrosis imaging, which comprises formulating a metal complex of claim 2 into a form suitable for infarction or necrosis imaging.

14. A method for the production of contrast media for use in radiodiagnosis or radiotherapy, which comprises formulating a metal complex of claim 3 into a form suitable for radiodiagnosis or radiotherapy.

15. A method for the production of contrast media for lymphography in the diagnosis of changes in the lymphatic system, which comprises formulating a metal complex of claim 2 into a form suitable for lympography.

16. A method for the production of contrast media for use in indirect lymphography, which comprises formulating a metal complex of claim 2 into a form suitable for indirect lympography.

17. A method for the production of contrast media for use in intravenous lymphography, which comprises formulating a metal complex of claim 2 into a form suitable for intravenous lympography.

18. A method for the production of contrast media for visualizing the vascular space, which comprises formulating a metal complex of claim 2 into a form suitable for visualizing the vascular space.

19. A method for the production of contrast media for tumor imaging, which comprises formulating a metal complex of claim 2 into a form suitable for tumor imaging.

20. A pharmaceutical composition comprising at least one physiologically compatible metal complex according to claim 1, optionally with the additives that are commonly used in galenicals.

21. Process for the production of perfluoroalkyl-containing complexes with polar radicals of formula I of claim 1:

(I)

in which K, G, R, Z, R$_f$, l, m and p have the meaning that is indicated in claim 1, which comprises reacting a carboxylic acid of formula IIa

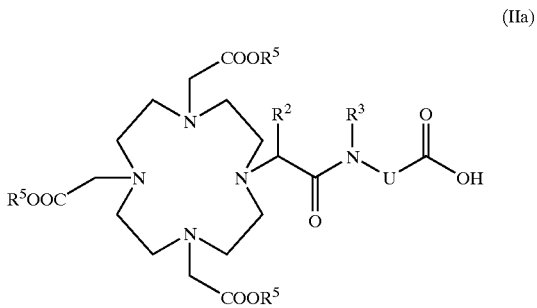

(IIa)

in which R$^5$ is a metal ion eqivalent of atomic numbers 21–29, 31–33, 37–39, 42–44, 49 or 57–83 or a carboxyl protective group, and R$^2$, R$^3$ and U have the abovementioned meaning, or a carboxylic acid of formula IIIa

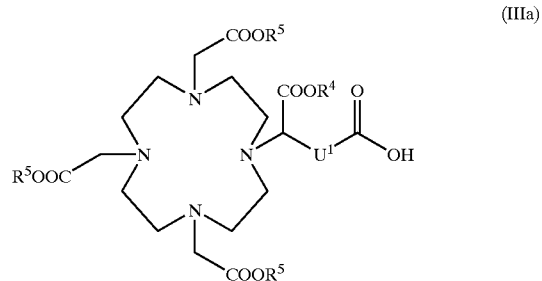

(IIIa)

in which R$^4$, R$^5$, and U$^1$ have the above-mentioned meaning or a carboxylic acid of formula IVa

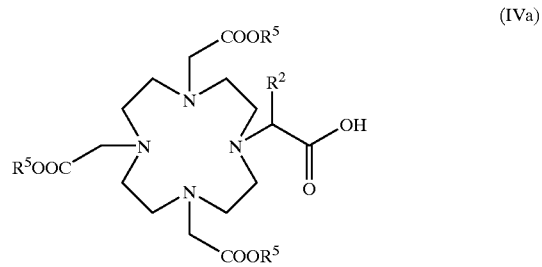

(IVa)

in which R$^5$ and R$^2$ have the above-mentioned meaning or a carboxylic acid of formula Va or Vb

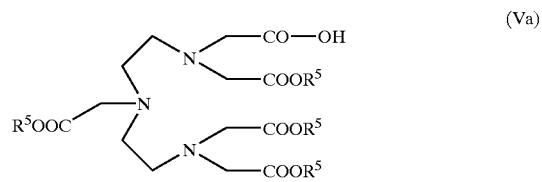

(Va)

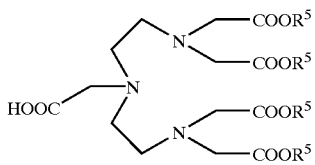

in which $R^5$ has the above-mentioned meaning or a carboxylic acid of formula VIa

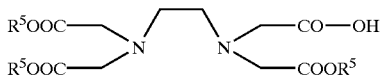

in which $R^5$ has the above-mentioned meaning or a carboxylic acid of formula VIIa

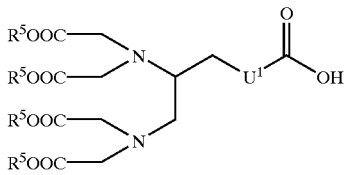

in which $R^5$ and $U^1$ have the above-mentioned meanings, optionally activated form, with an amine of formula VIII

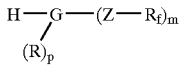

in which G, R, Z, $R_f$, m and p have the indicated meaning, in a coupling reaction and optionally subsequently cleaving optionally present protective groups to provide a metal complex of formula I, or if $R^5$ is a protective group, reacting after cleavage of these protective groups in a subsequent step with at least one metal oxide or metal salt of an element of atomic numbers 21–29, 31–33, 37–39, 42–44, 49 or 57–83, and then optionally present acidic hydrogen atoms are optionally substituted by cations of inorganic and/or organic bases, amino acid or amino acid amides.

22. Metal complexes according to claim 1, wherein polar radical R has one of the following meanings:

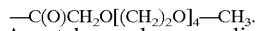

23. A metal complex according to claim 1, wherein metal ion equivalent $R^1$ is a gadolinium(III), terbium(III), dysprosium(III), holmium(III), erbium(III), iron(III) or manganese(II) ion.

24. A metal complex according to claim 1, wherein K is of formula II, III, VB or VII.

25. A metal complex according to claim 1, wherein $R^2$ and $R^3$, independently of one another, hydrogen or $C_1$–$C_4$ alkyl.

26. A metal complex according to claim 1, wherein $R^2$ is methyl and $R^3$ is hydrogen.

27. A metal complex according to claim 1, wherein Rf is —$C_nF_{2n+1}$, where n is a number from 4–15.

28. A metal complex according to claim 1, wherein Rf is —$C_4F_9$, —$C_6F_{13}$, —$C_8F_{17}$, $C_{12}F_{25}$ or —$C_{14}F_{29}$.

29. A composition of claim 20, wherein the composition contains 0.1 $\mu$mol–2 mol/l of the metal complex.

* * * * *